(12) United States Patent  (10) Patent No.: US 8,889,851 B2
Leproust et al.  (45) Date of Patent: Nov. 18, 2014

(54) METHODS FOR THE SYNTHESIS AND PURIFICATION OF OLIGOMERS

(71) Applicant: Agilent Technologies, Inc., Loveland, CO (US)

(72) Inventors: Emily Marine Leproust, San Jose, CA (US); Jeremy Lackey, San Jose, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 0 days.

(21) Appl. No.: 13/670,220

(22) Filed: Nov. 6, 2012

(65) Prior Publication Data

US 2013/0137861 A1 May 30, 2013

Related U.S. Application Data

(60) Provisional application No. 61/565,465, filed on Nov. 30, 2011.

(51) Int. Cl.
    *C07H 21/00* (2006.01)
(52) U.S. Cl.
    USPC ............. 536/25.3; 536/25.32; 536/25.34; 536/25.4; 536/25.41; 560/8; 560/18
(58) Field of Classification Search
    None
    See application file for complete search history.

(56) References Cited

FOREIGN PATENT DOCUMENTS

WO    WO03062452    7/2003

OTHER PUBLICATIONS

Delft, et al., Oligonucleotide Conjugates by Means of Copper-Free Click Chemistry Expanding the Repertoire of Strained Cyclooctyne Phosphoramidlte. Synthesis, 2011, No. 17. pp. 2724-2732.
Delft, et al., Synthesis of Oligoribonucieic Acid Conjugates Using a Cyclooctne Phosphoramidite. Org. Lett, vol. 12, 2010. 5486-89.
Marks, et al., Strain-Promoted "Click" Chemistry for Terminal Labeling of DNA. Bioconjugate Chemistry, 2011, No. 22, 1259-63.
Singh, et al., Fast, copper-free click chemistry: a convenient solid-phase approach to oligonucleotide conjugation. ChemComm, 2009, 3276-78.
Seela, et al., 8-Aza-7-deazaguanine nucleosides and oligonucleotides with octadiynyl side chains: synthesis, functionalization by the azide-alkyne 'click' reaction and nucleobase specific fluorescence quenching of coumarin dye conjugates. Organic & Biomolecular Chemistry, 2009, No. 7, 1374-87.
Seela, et al., Nucleosides and Oligonucleotides With Diynyl Side Chains: The Huisgen-sharpless Cycloaddition "Click Reaction" Performed on DNA and Their Constituents. Nucleosides, Nucleotides, and Nucleic Acids, 2007, No. 26, 597-601.
Seela, et al., Pyrrolo-d'C oligonucleotides bearing alkynyl side chains with terminal triple bonds: synthesis, base pairing and fluorescent dye conjugates prepared by the azide-alkyne "click" reaction. Org. Biomol. Chem., 2008, No. 6,1674-87.
Shelbourne, et al., Fast copper-free click DNA ligation by the ring-strain promoted alkyne-azide cycloaddition reaction. Chem. Commun., 2011,No. 47, 6257-59.
Ustinov, et al., Perylene DIiMIDE-Oligonucleotide Conjugates Constructed by Click Chemistry. Nucleosides, Nurleotides, and Nucleic Acids, 2007, No. 26, 751-54.
European Search Report for EP Application No. 12190465, mailed on Mar. 28, 2013, 10 pages.
Amblard, et al., "Cu(I)-catalyzed Huisgen azide-alkyne 1,3-dipolar cycloaddition reaction in nucleoside, nucleotide, and oligonucleotide chemistry", Chem Rev, 2009, 109:4207-20.
Jewett, et al., "Cu-free click cycloaddition reactions in chemical biology", Chem Soc Rev, 2010, 39:1272-9.
Nwe, et al., "Growing applications of "click chemistry" for bioconjugation in contemporary biomedical research", Cancer Biother Radiopharm, 2009, 24:289-302.
Wenska, et al., "An activated triple bond linker enables 'click' attachment of peptides to oligonucleotides on solid support", Nucleic Acids Res, 2011, 39:9047-59.

*Primary Examiner* — Patrick Lewis

(57) ABSTRACT

A reagent for oligonucleotide synthesis or purification, wherein the reagent has a structure of:

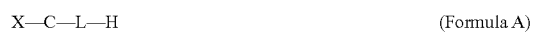

X—C—L—H  (Formula A)

wherein X is a phosphoramidite group, an H-phosphonate group, an acetal group, or an isocyanate; C is a direct bond or a cleavable adaptor represented by —$C_a$—$C_b$—; L is a hydrocarbyl chain; and H is a terminal alkyne or an activated cyclooctyne. The reagent of Formula (A) can be used in the synthesis and purification of oligonucleotides.

17 Claims, 7 Drawing Sheets

METHODS FOR THE SYNTHESIS AND PURIFICATION OF OLIGOMERS

BACKGROUND OF INVENTION

1. Field of the Invention

The present application relates generally to the field of reagents, synthesis and purification of oligonucleotides.

2. Background Art

Oligonucleotides are short nucleic acid polymers, typically containing from a few to several hundred nucleotides. They are important tools for genomic research and biotechnology. Although oligonucleotides can be generated by cleavage of longer precursors, they are now more commonly synthesized from monomers in a sequence-specific manner. They are typically synthesized on solid support using phosphoramidite chemistry or phosphonate chemistry.

FIG. 1A shows a typical synthetic cycle for solid phase oligonucleotide synthesis using phosphoramidites. The four major steps include: 1) Detritylation; 2) Coupling; 3) Capping; and 4) oxidation. As shown in FIG. 1, a first nucleotide is chemically bonded to a solid support (e.g., controlled pore glass beads). These can be purchased from commercial sources with the first nucleotide pre-coupled to the solid support.

To start the synthesis, the 5'-hydroxy protecting group (commonly used 5'-hydroxyl protection group is a trityl (i.e., —C(Ph)$_3$) or a 4,4'-dimethoxytrityl group, which may be abbreviated as DMT, DMTr) on the first nucleotide is removed using a mild acid (e.g., 2 or 3% trichloroacetic acid in an inert solvent, such as dichloromethane or toluene). Then, a 5'-DMTr-protected second nucleotide having a 3'-phosphoramidite group (e.g., 3'-O-(2-cyanoethyl-N—N-diisopropyl)phosphoramidite) is coupled to the free 5'-hydroxyl group on the first nucleotide on the solid support. The coupling can be achieved with activating the phosphoramidite using an acidic azole catalyst (e.g., 1H-tetrazole) in acetonitrile. The activated phosphoramidite then reacts with the free 5'-hydroxyl group to form a phosphite triester linkage.

Because the coupling reaction is never 100% efficient, some free 5'-hydroxyl group would remain. Any non-reacted 5'-hydroxyl group is capped with acetic anhydride and an acylation catalyst (e.g., N-methyl imidazole) to prevent the failure sequences from reacting in the next cycle. After capping, the phosphite triester is oxidized to convert it to a phosphate linkage. Oxidation can be accomplished with iodine in the presence of a weak base (e.g., pyridine). These steps complete the first coupling cycle. The processes can be repeated many cycles until the desired oligonucleotide is synthesized.

A similar method is illustrated in FIG. 1B, which uses H-phosphonate monomers instead of phosphoramidites. Most steps are similar, except that only one oxidation step is needed and is performed at the end of the synthesis.

At the completion of the chain elongation, the oligonucleotide is still attached to the solid support and is fully protected. To furnish a functional oligonucleotide, the protecting groups need to be removed and the oligonucleotide product needs to be released from the solid support. These can be accomplished using a base solution (e.g., ammonium hydroxide or aqueous methylamine) and perhaps other pretreatment steps (e.g., deprotection of 2-cyanoethyl protection group).

The above-described synthesis procedures are applicable for the synthesis of DNA or RNA oligomers. However, for RNA synthesis, the 2'-hydroxyl groups need to be protected with groups that can survive the reactions conditions. Typical 2'-hydroxy protecting groups include t-butyldimethylsilyl (TBDMS) and triisopropylsilyloxymethyl (TOM).

In general, the coupling step is never 100% complete. Incomplete reaction leads to the formation of short-mers. As noted above, the short-mers are typically capped off with a reagent, such as acetic anhydride, to prevent them from growing during iterative solid phase synthesis. This generally results in a pool of oligomers consisting of short-mers (n−1, n−2, n−3, etc. mers) and the desired full-length product. FIGS. 2A and 2B show an HPLC chromatogram and PAGE analysis, respectively, to illustrate the fact that the product is a mixture containing some failure sequences.

The products from oligonucleotide synthesis always contain failure sequences (shorter oligonucleotides, mostly n−1 mers). Traditionally, these crude products are purified using HPLC or gel electrophoresis, such as PAGE. Though these methods are acceptable for the purification of short oligonucleotides, they are unacceptable for the purification of longer oligonucleotides (e.g., 50-300-mers). In addition, these methods can be expensive and time consuming, can consume vast amounts of solvents, and can be limited to the use of trained professionals.

To facilitate the synthesis and purification of oligonucleotides, alternative approaches have been investigated, such as using synthetic purification handles to circumvent the use of HPLC or PAGE. Examples of these alternative methods include fluorous-affinity extraction (Beller, C.; Bannwarth, W., *Noncovalent Attachment of Nucleotides by Fluorous-Fluorous Interactions: Application to a simple Purification Principle for Synthetic DNA Fragments*, Helv. Chim. Acfa 2005, 88, pp. 171-179; WO 2006/081035 A2), biotin-avidin enabled affinity extraction (Fang, S.; Bergstrom, D. E., *Reversible Biotinylation of the 5'-Terminus of Oligodeoxyribonucleotides and its Application in Affinity Purification*, Current Protocols in Nucleic Acid Chemistry, John Wiley & Sons, Inc. 2001; Fang, S.; Bergstrom, D. E., *Reversible 5'-end Biotinylation and Affinity Purification of Synthetic RNA*, Tetrahedron Letters 2004, 45 (43), 7987-7990), and reaction-based extraction methods via Diels-Alder (WO 2003/062452 A2) and polymerization (U.S. Patent Publication No. 2008/0081902 A1).

The affinity-based methods (i.e., fluorous affinity extraction and biotin-avidin methods) require complex synthesis to generate the tagged-oligonucleotide handles, which can be costly. In the case of fluorous-affinity extraction, the fluorous-containing phosphorylating reagent couples too slowly to be used as a capping agent for long oligonucleotide synthesis. For use as the last monomer, the 5'-DMTr fluorous-modified phosphoramidite monomers are sparingly soluble in acetonitrile, and couple slowly and inefficiently. They also require a final acidic treatment, which may cause depurination and affect the integrity of long oligonucleotides. This strategy also requires a fluorous phase affinity column, which increases complexity and cost, and may not be amenable to high throughput or large scale purification.

Biotin-avidin enabled affinity extraction has not been widely used and has never been used as a capping reagent to trap failure sequences. The biotin phosphorylating reagents, or 5'-modified phosphoramidite monomers, are expensive to manufacture due to the cost of biotin itself. In addition, the biotin phosphoramidites (phosphorylating reagents and monomers) are not very soluble in acetonitrile and the recommended coupling times are slow (i.e., about 15 min). Thus, they are not useful as capping reagents. In addition, this method has not been shown to be useful for long oligonucleotides. Also, this method relies on biotin's affinity to streptavidin-beads, which are expensive in a high throughput or large scale platform.

Due to the costs and other issues with the affinity-based approach, alternative methods that have been examined, such as reaction-based methods. These methods include those using Diels-Alder and polymerization. In the Diels-Alder approach, a diene-phosphorylating reagent is used to cap the truncated sequences, which can then be later pulled out of the product mixtures via a 4+2 cycloaddition with a maleimide-containing solid support. In practice, this method is restricted to the purification of short oligonucleotides (less than 20-mer) and the final yield and purity is poor due to inefficient reactions.

The polymerization method uses an acrylamide phosphorylating reagent to cap off the truncated (failure) sequences. Upon completion of the synthesis, radical polymerization is initiated to form polymers, which can then be separated from the full-length product. Acrylamide phosphoramidite monomers have also been used as the last nucleotide in a chain and the full-length products can be trapped by radical polymerization, thereby separating them from the short-mers, which do not contain an acrylamide moiety. Again, this method is practical for short oligonucleotides, e.g., less than 20-mers, and there is concern that radical polymerization may alter the integrity of the desired oligonucleotide due to side-reactions. Furthermore, the overall purity and recovery of the desired full-length products are less than optimal. Therefore, this method may not be suitable for high throughput purification or large scale production.

While these prior art methods are useful in some situations, there remains a need for better methods for the synthesis and purification of oligonucleotides.

SUMMARY OF INVENTION

One aspect of the invention relates to A reagent for oligonucleotide synthesis or purification, wherein the reagent has a structure of:

  (Formula A)

wherein
X is a functional group that can react with the 5'-hydroxyl group on a nucleoside, nucleotide, oligonucleotide, or the like, to form a stable bond that would survive the iterative nucleotide coupling cycles, the deprotection and the cleavage reactions of oligonucleotide synthesis; Suitable X functional groups may include phosphoramidite, H-phosphonate, acetal, isocyanate, etc
C is a direct bond or a cleavable adaptor wherein the cleavable adaptor is represented by —$C_a$—$C_b$—, wherein $C_a$ is connected to X and is a direct bond, hydrocarbyl, aryl, heteroaryl, cycloalkyl, heterocyclyl, a nucleoside, each of which is optionally substituted with one to two substituents selected from halo, hydroxyl, ($C_1$-$C_6$) alkoxy, ($C_1$-$C_6$) alkyl, amino or alklyamino; $C_b$ is a direct bond, a silanyl group, a trityl group, or a vicinyl alcohol group. Preferably $C_a$ is a direct bond, ($C_1$-$C_{12}$)hydrocarbyl, ($C_6$-$C_{12}$)aryl, 5- to 12-membered heteroaryl, ($C_3$-$C_{12}$)cycloalkyl, 4- to 12-membered heterocyclyl, a nucleoside;
L is a hydrocarbyl chain which may be optionally substituted with one to four substituent groups independently selected from the group consisting of 5-to 9-membered heteroaryl, 4- to 9-membered heterocyclyl, amino, ether, carboxyl, carbamoyl, ($C_6$-$C_{12}$)aryl, —O—R", O—CO—R", —NR'—R", —NR'—CO—R", CO—NR'—R", —CO—R", —CN, halogen, or a combination thereof, wherein R' and R" are independently H or ($C_1$-$C_6$)hydrocarbyl; Preferably L is hydrocarbyl such as ($C_1$-$C_{12}$)alkyl, ($C_2$-$C_{12}$)alkenyl, or ($C_2$-$C_{12}$) alkynyl, each of which may be optionally substituted with one to two substituent groups selected from amino, ether, carboxyl, carbamoyl, or halogen;
Or L may be a hydrocarbyl chain interspersed with other atoms, as represented by —(CHR')$_a$—$W_b$—(CHR')$_c$—$V_d$—(CHR')$_e$—, wherein W and V are independently 0, S, or —NR'—; R' is H or ($C_1$-$C_6$)alkyl; and a, b, c, d, and e are independently an integer from 0 to 10, preferably from 0 to 6, or preferably from 0 to 3, and the sum of a, b, c, d, and e is preferably an integer from 2 to 6.
H is a "click handle," as defined above and may include a terminal alkyne or an activated cyclooctyne.

One aspect of the invention relates to activated cyclooctyne compounds. A activated cyclooctyne compound in accordance with one embodiment of the invention has a structure shown in Formula (I):

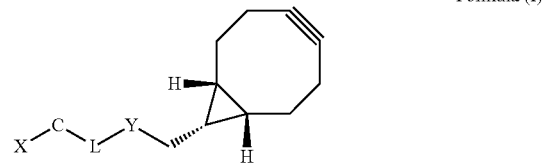

wherein Y is a linkage functional group selected from —O—, —S—, —NR'—, —NH—CO—O, —O—CO—NH—, —NH—CO—NH—, wherein R' is hydrogen or a lower alkyl (e.g., ($C_1$-$C_3$)alkyl or ($C_1$-$C_6$)alkyl); X, C, and L are as defined above.

One aspect of the invention relates to compounds of Formula (I), wherein X includes a phosphoramidite. These compounds have the general structure shown in Formula (II):

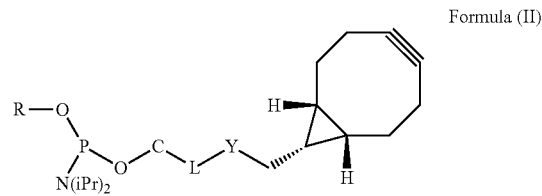

wherein the linker L, C, and Y are as defined above and R is ($C_1$-$C_6$)alkyl or cyanoethyl. The phosphoramidite group can react with a hydroxyl group to form a phosphate linkage that is stable under the conditions for the synthesis and deprotection of oligonucleotides.

One aspect of the invention relates to compounds of Formula (I), wherein X includes an H-phosphonate. These compounds have the general structure shown in Formula (III):

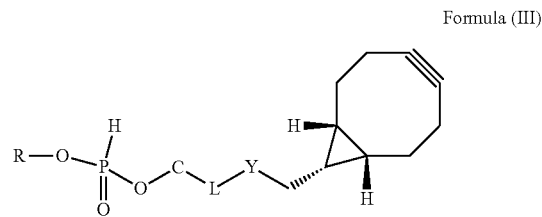

wherein the linker L, Y, C, and R are as defined above. The H-phosphonate group can react with a hydroxyl group to form a phosphate linkage that is stable under the conditions for the synthesis and deprotection of oligonucleotides.

One aspect of the invention relates to compounds of Formula (I), wherein X includes an isocyanate group. These compounds have the general structure shown in Formula (III):

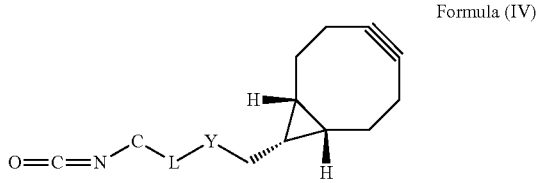

Formula (IV)

wherein the linker L, Y, and C are as defined above. The cyanate group can react with a hydroxyl group to form a carbamate linkage that is stable under the conditions for the synthesis and deprotection of oligonucleotides.

One aspect of the invention relates to compounds of Formula (II) having the structures shown below:

Some embodiments of the invention may further comprise the steps of:
(e) deprotecting a 5'-hydroxy protecting group on the intermediate polynucleotide; and
(f) coupling a final nucleotide monomer to the intermediate polynucleotide to produce a final polynucleotide.

Some embodiments of the invention may further comprise the steps of:
(g) deprotecting and cleaving the final polynucleotide from the solid support to produce a product mixture;
(h) reacting a solution of the product mixture with an azide-containing solid support or a nitrone-containing solid support; and
(i) separating the solution containing the polynucleotide from the azide-containing or nitrone-containing solid support.

(Compound 1)

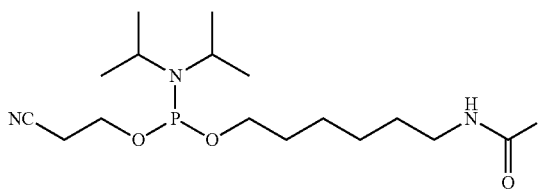

(Compound 2)

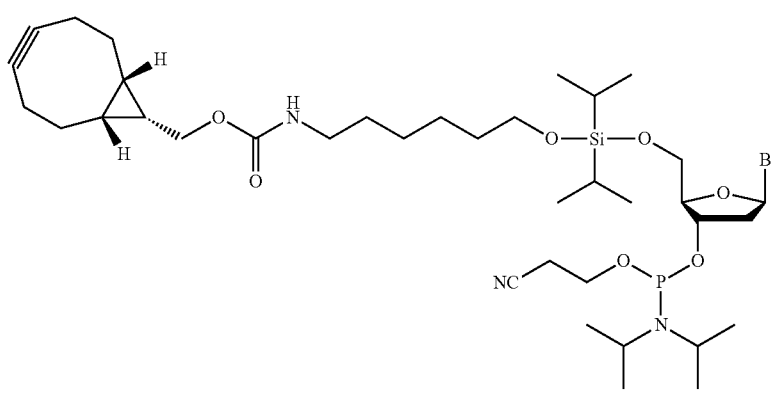

(Compound 3)

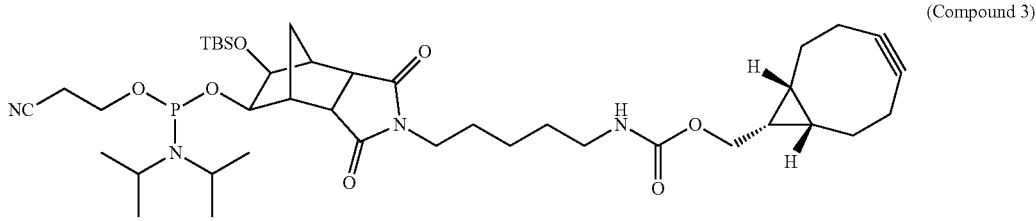

One aspect of the invention relates to methods for synthesizing polynucleotides. A method in accordance with one embodiment of the invention may include the following steps:
(a) deprotecting a 5'-hydroxy protecting group of an oligonucleotide on a solid support to produce a free 5'-hydroxy group of the oligonucleotide on the solid support;
(b) coupling a nucleotide monomer, which contains a 5'-hydroxy protecting group, to the free 5'-hydroxy group of the oligonucleotide on the solid support via a 3'-phosphorous containing group on the nucleotide monomer;
(c) capping unreacted 5'-hydroxy group of the oligonucleotide on the solid support using the reagent of Formula (A); and
(d) repeating steps (a)-(c) for a selected number of times to produce an intermediate polynucleotide on the solid support.

A method for synthesizing a polynucleotide in accordance with another embodiment of the invention may include the following steps:
(a) deprotecting a 5'-hydroxy protecting group of an oligonucleotide on a solid support to produce a free 5'-hydroxy group of the oligonucleotide on the solid support;
(b) coupling a nucleotide monomer, which contains a 5'-hydroxy protecting group, to the free 5'-hydroxy group of the oligonucleotide on the solid support via a 3'-phosphorous containing group on the nucleotide monomer;
(c) capping unreacted 5'-hydroxy group of the oligonucleotide on the solid support using a capping reagent;
(d) repeating steps (a)-(c) for a selected number of times to produce an intermediate polynucleotide on the solid support;
(e) deprotecting a 5'-hydroxy protecting group on the intermediate polynucleotide; and (f) coupling a final nucleotide monomer to the intermediate polynucleotide to produce a final polynucleotide, wherein the final nucleotide monomer contains the reagent of Formula (A).

Some embodiments of the invention may further comprise the steps of:

(g) deprotecting and cleaving the final polynucleotide from the solid support to produce a product mixture;
(h) reacting a solution of the product mixture with an azide-containing solid support or a nitrone-containing solid support to produce a full-length polynucleotide bonded to the solid support; and
(i) isolating the full-length polynucleotide bonded to the azide-containing or nitrone-containing solid support.

The method may further include releasing the full length polynucleotide from the azide-containing or nitrone-containing solid support. Some embodiments of the invention may further include purification of the released full length polynucleotides.

Other aspects and advantages of the invention will be apparent from the following description and the appended claims.

BRIEF DESCRIPTION OF DRAWINGS

FIG. 2 panel B shows a schematic illustrating a method of the invention for the synthesis and purification of a polynucleotide using the reagent of FIG. 2 panel A.

FIG. 3 panel B shows a schematic illustrating a method of the invention for the synthesis and purification of a polynucleotide using the reagents of FIG. 3 panel A.

DETAILED DESCRIPTION

Figure 1A:
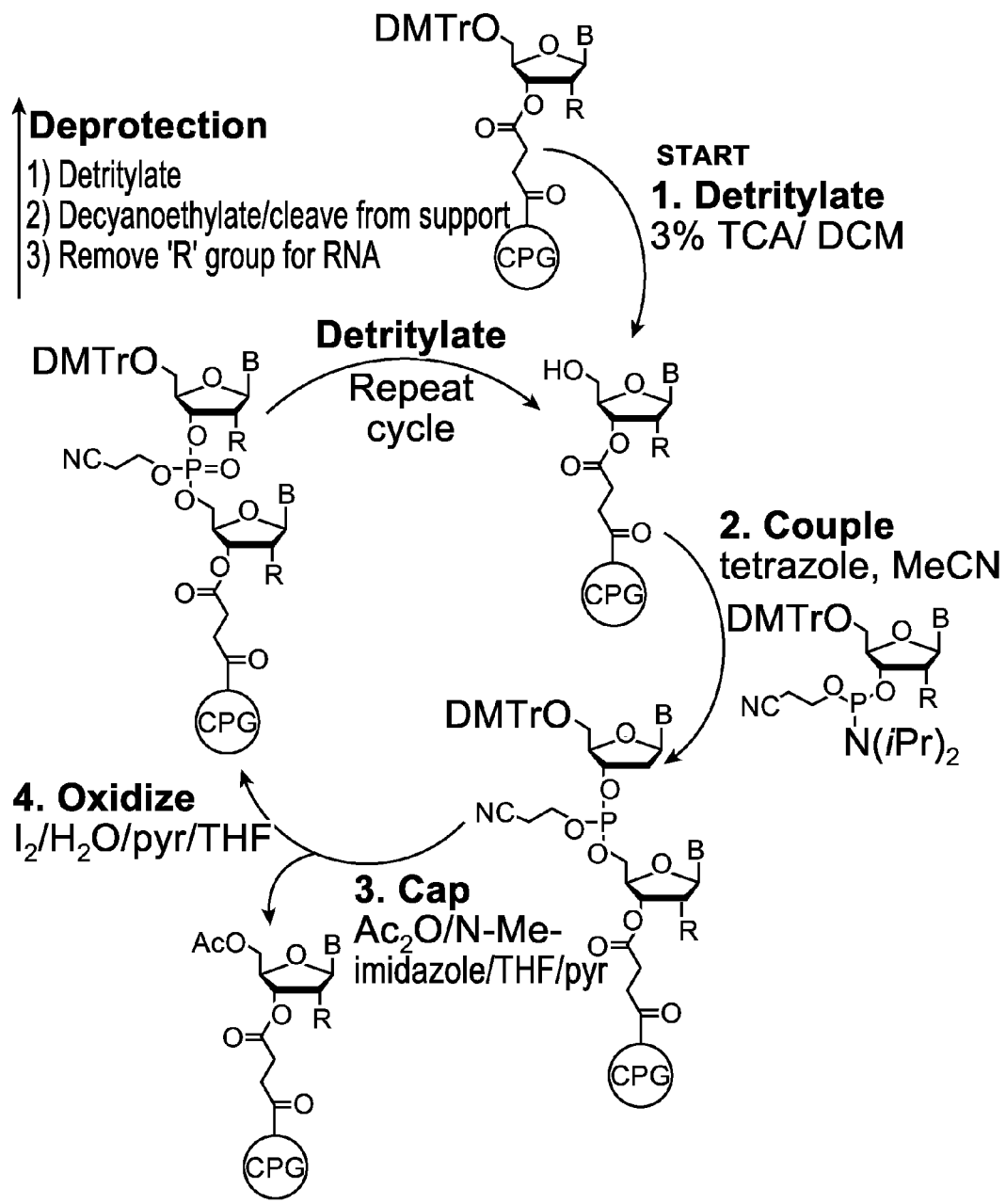
FIG. 1A shows a conventional phosphoramidite method for the synthesis of a polynucleotide on a solid support. The method includes four steps: deprotection; coupling; capping; and oxidation.
Figure 1B:
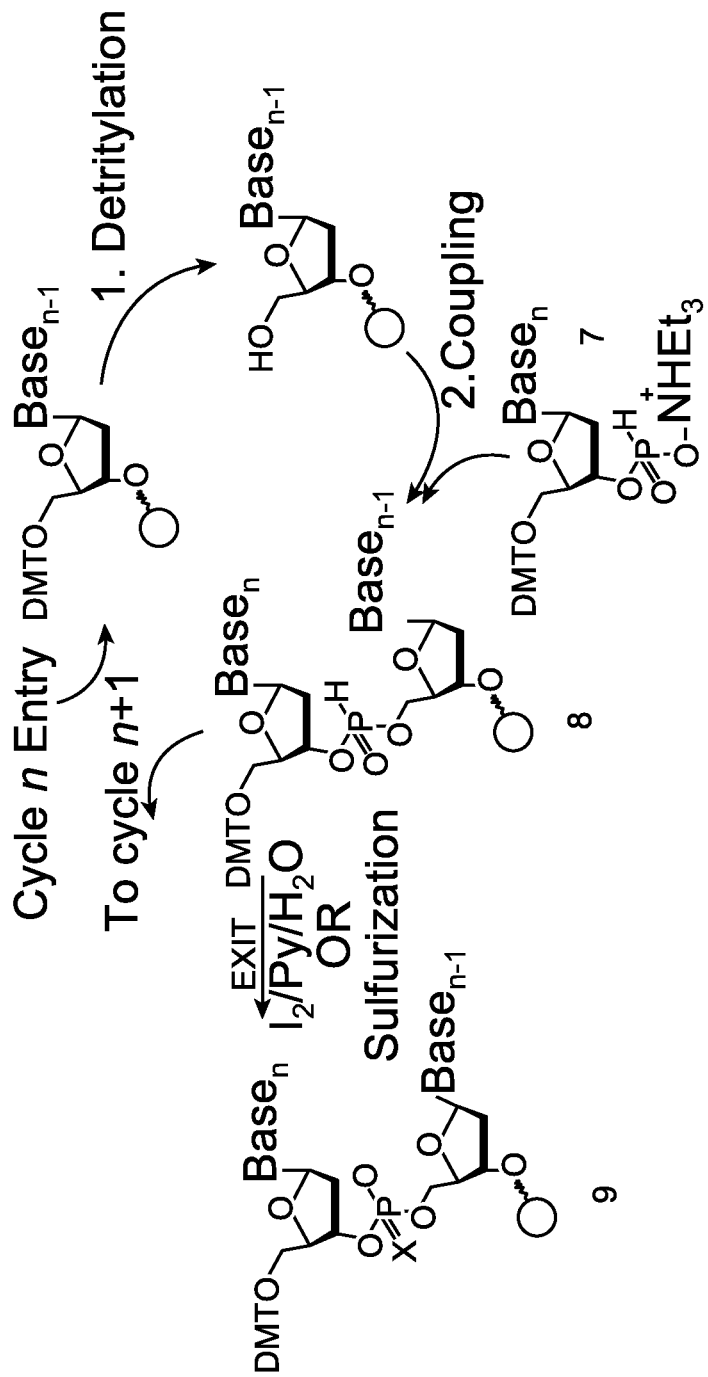
FIG. 1B shows a conventional H-phosphonate method for the synthesis of a polynucleotide on a solid support.

Embodiments of the invention relate to novel terminal alkyne or activated cyclooctyne reagents and methods for the synthesis and purification of oligonucleotides. The novel terminal alkyne or activated cyclooctyne reagents may include a function group that is reactive with a hydroxyl group to form a bond that this stable under the conditions for the synthesis and deprotection of a polynucleotide. The function group may include a phosphoramidite group, an H-phosphonate group, an acetal group, or an isocyanate group. Methods of the invention use the novel terminal alkyne or activated cyclooctyne reagents and "click" chemistry to facilitate the purification of oligonucleotide products. While embodiments of the invention are most advantageous with relatively long oligonucleotides (e.g., 50-mers or longer), one skilled in the art would appreciate that the benefits of embodiments of the invention can be realized with any oligonucleotides, including short oligonucleotides.

A "polynucleotide", "oligonucleotide" or a "nucleic acid" refers to a compound containing a plurality of nucleoside moiety subunits or nucleoside residues that are linked by internucleotide bonds. As such it also refers to a compound containing a plurality of nucleotide moiety subunits or nucleotide residues.

A "nucleoside monomer" is a nucleoside which is not part of a polynucleotide. A nucleoside monomer may also contain such groups as may be necessary for an intended use of the nucleoside monomer. A nucleoside monomer may be free or attached to a solid support. For example, a nucleoside monomer having a heterocyclic base protecting group and one or more hydroxyl protecting groups may be a synthetic intermediate in the synthesis of a nucleotide monomer. For example, a nucleoside monomer may be attached to a solid support for the synthesis of a polynucleotide.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases or nucleobases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, N,N-diphenyl carbamate, substituted thiourea or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-methylguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars and conventional stereoisomers, but other sugars as well, including L enantiomers and alpha anomers. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides or oligonucleotides incorporating non-natural (not usually occurring in nature) nucleotides, unnatural nucleotide mimetics such as 2'-modified nucleosides including but not limited to 2'-fluoro, 2'-O-alkyl, O-alkylamino, O-alkylalkoxy, protected O-alkylamino, O-alkylaminoalkyl, O-alkyl imidazole, and polyethers of the formula (O-alkyl)m such as linear and cyclic polyethylene glycols (PEGs), and (PEG)-containing groups, locked nucleic acids (LNA), peptide nucleic acids (PNA), oligomeric nucleoside phosphonates, and any polynucleotide that has added substituent groups, such as protecting groups or linking groups.

The term "phosphoramidite group" refers to a group comprising the structure —P(OR$^{13}$)(NR$^{14}$R$^{15}$), wherein each of R$^{13}$, R$^{14}$, and R$^{15}$ is independently a hydrocarbyl, substituted hydrocarbyl, heterocycle, substituted heterocycle, aryl or substituted aryl. In some embodiments, R$^{13}$, R$^{14}$, and R$^{15}$ may be selected from lower alkyls, lower aryls, and substituted lower alkyls and lower aryls (preferably substituted with structures containing up to 18, 16, 14, 12, 11, 10, 9, 8, 7, 6, 5, 4, 3 or 2 carbons). In some embodiments, R$^{13}$ is 2-cyanoethyl or methyl, and either or both of R$^{14}$ and R$^{15}$ is isopropyl. R$^{14}$ and R$^{15}$ can optionally be cyclically connected.

The term "H-phosphonate" refers to a group comprising the structure —P—(O)(H)(OR$^{16}$), wherein R$^{16}$ is H, acyl, substituted acyl, hydrocarbyl, substituted hydrocarbyl, heterocycle, substituted heterocycle, aryl or substituted aryl. In some embodiments, R$^{16}$ may be selected from lower alkyls, lower aryls, and substituted lower alkyls and lower aryls (preferably substituted with structures containing up to 18, 16, 14, 12, 11, 10, 9, 8, 7, 6, 5, 4, 3 or 2 carbons). In some embodiments, R$^{16}$ is pivaloyl or adamantoyl.

The term "alkyl" as used herein, unless otherwise specified, refers to a saturated straight chain, branched or cyclic hydrocarbon group of 1 to 24 (i.e., ($C_1$-$C_{24}$)alkyl), typically 1-12 (i.e., ($C_1$-$C_{12}$)alkyl) carbon atoms, more typically 1-6 carbon atoms (i.e., ($C_1$-$C_6$)alkyl), such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

"Alkylene" and "alkylene chain" refer to a straight or branched divalent hydrocarbon chain, linking the rest of the molecule to a radical group, consisting solely of carbon and hydrogen, containing no unsaturation and having from one to twelve carbon atoms, preferably having from one to eight carbons, e.g., methylene, ethylene, propylene, n-butylene, and the like. The alkylene chain may be attached to the rest of the molecule and to the radical group through one carbon within the chain or through any two carbons within the chain.

Moreover, the term "alkyl" includes "modified alkyl", which references an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl.

Similarly, the term "lower alkyl" includes "modified lower alkyl", which references a group having from one to eight carbon atoms and further having additional groups, such as one or more linkages selected from ether-, thio-, amino-, phospho-, keto-, ester-, and amido-, and/or being substituted with one or more groups including lower alkyl; aryl, alkoxy, thioalkyl, hydroxyl, amino, sulfonyl, thio, mercapto, imino, halo, cyano, nitro, nitroso, azide, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of C5 and C6) hydrocarbon group of 2 to 24 (i.e., ($C_2$-$C_{24}$)alkenyl), typically 2 to 12 (i.e., ($C_2$-$C_{12}$)alkenyl) carbon atoms, more typically 2-6 carbon atoms (i.e., ($C_2$-$C_6$)alkenyl), containing at least one double bond, such as ethenyl, vinyl, allyl, octenyl, decenyl, and the like. The term "lower alkenyl" intends an alkenyl group of two to eight carbon atoms, and specifically includes vinyl and allyl. The term "cycloalkenyl" refers to cyclic alkenyl groups.

"Alkenylene" and "alkenylene chain" refer to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to eight carbon atoms, and includes, for example, acetylenyl and propynyl, and the term "cycloalkynyl" refers to cyclic alkynyl groups.

The term "hydrocarbyl" refers to alkyl, alkylene, alkenyl, alkenylene, or alkynyl. The number of carbon atoms in a hydrocarbyl group may be indicated, for example, as "($C_1$-$C_{12}$)hydrocarbyl," which denotes a hydrocarbyl containing from 1 to 12 carbon atoms. A hydrocarbyl group having different numbers of carbon atoms may be indicated in a similar notation. The term "substituted hydrocarbyl" refers to hydrocarbyl moieties having substituents replacing a hydrogen on one or more carbons of the hydrocarbon backbone. Such substituents may include, for example, a hydroxyl, a halogen, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like.

The term "alkoxy" means an alkyl group linked to oxygen and may be represented by the formula: R—O—, wherein R represents the alkyl group as defined above. An example is the methoxy group $CH_3O$—. The term "$(C_1-C_6)$alkoxy" refers to an alkoxy radical as defined above containing one to six carbon atoms. Alkoxy containing different numbers of carbons will be denoted in a similar notation, e.g., $(C_1-C_3)$ alkoxy, $(C_1-C_{12})$alkoxy, $(C_3-C_{12})$alkoxy, etc.

"Aryl" refers to aromatic monocyclic or multicyclic, some of which may be fused together, hydrocarbon ring system consisting only of hydrogen and carbon and containing from 6 to 19 carbon atoms (represented as $(C_6-C_{19})$aryl), preferably 6 to 10 carbon atoms (represented as $(C_6-C_{10})$aryl), where the ring system may be partially or fully saturated. Aryl groups include, but are not limited to groups such as fluorenyl, phenyl and naphthyl. Unless stated otherwise specifically in the specification, the term "aryl" is meant to include aryl radicals optionally substituted by one or more substituents selected from $(C_1-C_{12})$hydrocarbyl, —O—R", —O—CO—R", —CO—O—R", —NR'—R", —NR'—CO—R", —CO—NR'—R", —CO—R", —R—O—R", —R—O—CO—R", —R—CO—O—R", —R—NR'—R", —R—NR'—CO—R", —R—CO—NR'—R", —R—CO—R", —CN, halogen, or a combination thereof, wherein R' and R" are independently H or $(C_1-C_{12})$hydrocarbyl, and R is $(C_1-C_{12})$hydrocarbyl.

"Heteroaryl" refers to a 5- to 18-membered monocyclic- or bicyclic- or fused polycyclic-ring system which consists of carbon atoms and from one to five heteroatoms selected from the group consisting of nitrogen, oxygen and sulfur. Preferably heteroaryl is a 5- to 12- or 5- to 9-membered ring system. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from $(C_1-C_{12})$hydrocarbyl, —O—R", —O—CO—R", —CO—O—R", —NR'—R", —NR'—CO—R", —CO—NR'—R", —CO—R", —R—O—R", —R—O—CO—R", —R—CO—O—R", —R—NR'—R", —R—NR'—CO—R", —R—CO—NR'—R", —R—CO—R", —CN, halogen, or a combination thereof, wherein R' and R" are independently H or $(C_1-C_{12})$hydrocarbyl, and R is $(C_1-C_{12})$hydrocarbyl.

The term "heteroaryl" also refers to a group in which a heteroaromatic ring is fused to one or more aryl, cycloaliphatic, or heterocyclyl rings, where the radical or point of attachment is on the heteroaromatic ring. Nonlimiting examples include but are not limited to 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinolyl, 1-, 3-, 4-, 5-, 6-, 7-, or 8-isoquinolyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]-pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl. Typical fused heteroary groups include, but are not limited to 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, 2-, 4-, 5-, 6-, or 7-benzothiazolyl.

"Cycloalkyl" refers to a stable non-aromatic monocyclic or bicyclic hydrocarbon radical consisting solely of carbon and hydrogen atoms, having from three to fifteen carbon atoms, preferably having from three to twelve carbon atoms, $(C_3-C_{12})$cycloalkyl, and which is saturated or unsaturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents selected from —O—R", —O—CO—R", —CO—O—R", —NR'—R", —NR'—CO—R", —CO—NR'—R", —CO—R", —CN, halogen, or a combination thereof, wherein R' and R" are independently H or $(C_1-C_{12})$ hydrocarbyl.

"Heterocyclyl" or "heterocycle" refers to an optionally substituted, saturated or partially unsaturated, nonaromatic cyclic group, e.g., which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2, 3, or 4 heteroatoms selected from nitrogen atoms, oxygen atoms and sulfur atoms, wherein the nitrogen and sulfur heteroatoms may also optionally be oxidized. The heterocyclic group may be attached at a heteroatom or a carbon atom. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. The bicyclic and tricyclic heterocyclyl groups can be fused or spiro rings or ring groups. Preferably heterocyclyl is a 4- to 12-membered ring system. Also preferably heterocyclyl is a 4- to 9-membered ring system.

Exemplary monocyclic heterocyclic groups include oxetanyl, thiatanyl, azetidinyl, dihydrofuranyl, tetrahydrofuranyl, dihydrothiophenyl, tetrahydrothiophenyl, pyrrolidinyl, dihydropyrazolyl, tetrahydropyrazolyl, dihydropyridinyl, tetrahydropyridinyl, dihydrothiopyranyl, tetrahydrothipyranyl, pyranyl, dihydropyranyl, tetrahydropyranyl, thiopyranyl, dihydrothiopyranyl, tetrahydrothiopyranyl, ptperidinyl, piperazinyl, morpholinyl, azepinyl, dihydroazepinyl, tetrahydroazepinyl, 2-oxopiperazinyl, 2-oxopiperidinyl, 2-oxopyrrolodinyl, 2-oxoazepinyl, oxepanyl, thiepanyl, dihyrothiepinyl, tetrahydrothiepinyl, dihydrooxepinyl, tetrahydrooxepinyl, 1,4-dioxanyl, 1,4-oxathianyl, morphoiinyl, oxazolyl, oxazolidinyl, isoxazolinyi, A-ptperidony!, isoxazoiinyi, isoxazolyl, 1,4-azathianyl, 1,4-oxathiepanyl, 1,4-oxaazepanyl, 1,4-dithiepanyl, 1,4-thieaxepanyl, 1,4-diazepanyl, tropanyl, 3,4-dihydro-2H-pyranyl, 5,6-dihydro-2H~pyranyl, thiazolidinyl, thiamorpholinyl, thiamorpholinyl sulfoxide, thiamorpholinyl sulfone, 1,3-dioxolane and tetrahydro-1,1-dioxothienyl, 1,1,4-trioxo-1,2,5-thiadiazolidin-2-yl, pyrazolinyl, and the like.

Exemplary bicyclic heterocyclic groups include but are not limited to, dihydroindolyl, quinuctidinyl, tetrahydroquinolinyl, decahydroquinolinyl, 2-oxa-6-azaspiro[3,3]heptan-6-yl, tetrahydroisoquinoiinyl, decahydroisoquinoiinyl, dihydroisoindolyl, indoiinyl, norboranyl, adamantanyl, and the like.

Unless stated otherwise specifically in the specification, the term "heterocyclyl" is meant to include heterocyclyl radicals as defined above which are optionally substituted by one or more substituents selected from —O—R", —O—CO—R", —CO—O—R", —NR'—R", —NR'—CO—R", —CO—NR'—R", —CO—R", —CN, halogen, or a combination thereof, wherein R' and R" are independently H or ($C_1$-$C_{12}$) hydrocarbyl.

The terms "halogen" and "halo" refer to a fluoro, chloro, bromo, or iodo moiety.

The term "acetal" has its general meaning in chemistry and have a formula: R—CH(OR')$_2$, wherein R' is an alkyl. Examples of acetals include R—CH(OCH$_3$)$_2$ and R—CH(OCH$_2$CH$_3$)$_2$.

The term "trityl" refers to —C(Ph)$_3$ or 4,4'-dimethoxytrityl group, which may be abbreviated as DMT or DMTr, or an analog of C(Ph)$_3$ or DMT having one or more substitutions on the one or more aromatic rings.

The term "isocyante" is used in its common meaning. An isocyanate has a general form a of: R—N=C=O, wherein R is residue for the remainder of the molecule. An isocyanate can react with an alcohol to form a carbamate, which is stable to conditions for the repetitive coupling and deprotection in the synthesis of an oligonucleotide.

The term "direct bond" means that the two entities linked by the "direct bond" are connected to each other directly.

The term "RNA", or "ribonucleic acid" refers to a polynucleotide or oligonucleotide which comprises at least one ribonucleotide residue.

As used herein, "click chemistry" or "click reaction" refers to the class of reactions that are very efficient and selective and can be used to stitch molecules together in high yields, as originally described by Sharpless and coworkers in 2001 (see discussion below). A "click reaction" typically involves a terminal alkyne or an activated alkyne analogs (such as activated cyclooctynes) and an azide or a nitrone.

As used herein, a "click handle" refers to a group that can participate in a "click reaction." A "click handle" is a terminal alkyne (—C≡CH) or an activated cyclooctyne, which may optionally contain a short linkage to connect with other parts of the molecule and may be optionally substituted with a substituent group. The short linkage may be an alkylene (e.g., ($C_1$-$C_6$)alkylene), an alkenylene (e.g., ($C_2$-$C_6$)alkenylene), an alkynylene (e.g., ($C_2$-$C_6$)alkynylene), —O—, —S—, —NR'—, —CO—NR'—, —NR'—CO—, —NR'—CO—O—, —O—CO—NR'—, —CO—, —CO—O—, —O—CO—, or a combination thereof, wherein R' is H or ($C_1$-$C_6$)alkyl. The optional substituent group may be —O—R", —O—CO—R", —NR'—R", —NR'—CO—R", —CO—NR'—R", —CO—R", —CN, halogen, or a combination thereof, wherein R' and R" are independently H or ($C_1$-$C_6$)alkyl.

The term "activated cyclooctyne" refers to a cyclooctyne that is activated by having one or more adjacent aromatic rings, having one or more fluorine substitutions (e.g., difluorocyclooctyne), or having one or more ring fusions that cause strain on the cyclooctyne ring. The ring fusions that can cause strain on the cyclooctyne ring typically involve small rings, such as a cyclopropyl or cyclobutyl ring. These various activated cyclooctynes are known in the art, as described below.

As used herein, a "linker" bridges two moieties in a molecule. A "linker" may be a hydrocarbyl chain (e.g., ($C_1$-$C_{12}$) alkylene, ($C_2$-$C_{12}$)alkenylene), optionally substituted with a substituent group, or a linker may be a hydrocarbyl chain interspersed with other atoms, as represented by —(CHR')$_a$—W$_b$—(CHR')$_c$—V$_d$—(CHR')$_e$—, wherein W and V are independently —O—, —S—, or —NR'—; R' is H or ($C_1$-$C_6$) alkyl; and a, b, c, d, and e are independently an integer from 0 to 10, preferably from 0 to 6, or preferably from 0 to 3, and the sum of a, b, c, d, and e is preferably an integer from 2 to 6. The optional substituent group may be —O—R", —O—CO—R", —NR'—R", —NR'—CO—R", —CO—NR'—R", —CO—R", —CN, halogen, or a combination thereof, wherein R' and R" are independently H or ($C_1$-$C_6$) hydrocarbyl.

As used herein, a "cleavable adaptor" is a moiety that contains a functional group that can be used to separate the "X" and "H" moieties in Formula (A): X—C—L—H. A "cleavable adaptor" contains a cleavable group, selected from a silanyl group, a trityl group, or a vicinyl alcohol, attached to a hydrocarbyl group (e.g., ($C_1$-$C_{12}$)hydrocarbyl), an aryl group (e.g., ($C_6$-$C_{18}$)aryl), a heroaryl group, a cycloalkyl (e.g., ($C_3$-$C_{12}$)cycloalkyl), or a combination thereof.

Examples of such "cleavable adaptors" include the 5'-silanyl-O-nucleoside group in Compound 2, the 5'-trityl-O-nucleoside group in Compound 4, and the vicinyl alcohol-containing norboranyl imide group in Compound 3, which are described below. The silanyl group as shown in Compound 2 can be cleaved with mild acid or fluoride, which is well known in the art. The trityl group can be cleaved with mild acid, which well known in the art. The vicinyl alcohols in the norborane structure as shown in Compound 3 (after removal of the TBS protection group) will undergo intramolecular trans-esterification/hydrolysis to hydrolyze the neighboring phosphate group. Note that the "cleavable adaptor" may include a nucleoside moiety or a similar moiety that would be left on the oligonucleotide products after the cleavage. Examples of these "cleavable adaptors" are shown in Compound 2 and Compound 4.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present.

K. Barry Sharpless and coworkers in 2001 coined the term, "click chemistry," to refer to a class of efficient and selective reactions that could be used to easily stitch molecules together in high yields. (Kolb et al., "*Click Chemistry: Diverse Chemical Function from a Few Good Reaction*," Ang. Chemie, Int'l Ed., 40, pp. 2004-21) The term "click" signifies the ease of joining molecular pieces as in "clicking" together two pieces of a buckle.

In 2002, Sharpless and Meldal groups independently demonstrated copper-catalyzed azide-alkyne cycloadditions, using organic azides and terminal acetylenes. (Rostovtsev et al., (2002) "A *Stepwise Huisgen Cycloaddition Process: Copper(I)-Catalyzed Regioselective 'Ligation' of Azides and Terminal Alkynes*," Ang. Chemie, Int'l Ed., 41, pp. 2596-99; Tornoe et al. (2002), "*Peptidotriazoles on Solid Phase: [1,2,3]-Triazoles by Regiospecific Copper(I)-Catalyzed 1,3-Dipolar Cycloadditions of Terminal Alkynes to Azides*," J. Organic Chem., 67, pp. 3057-64). The cyclic products are 1,4-substituted triazoles. The copper catalyst allows the reaction to proceed at room temperature and confers regioselectivity. However, copper is cytotoxic. Therefore, this reaction cannot be used in many situations. In response to this, other types of azide-alkyne cycloadditions have been developed that do not require copper as a catalyst. On approach is to increase the reactivities of alkynes by introducing ring strains, e.g., cyclooctynes.

Bertozzi was the first to describe the use cyclooctyne in azide-alkyne cycloadditions. (Jewett and Bertozzi, "*Cu-free click cycloaddition reactions in chemical biology*," Chem. Soc. Rev., 2010, 39, 1272-1279; and references cited therein). However, the reaction between an organic azide and cyclooctyne is sluggish compared to the copper catalyzed reaction. To circumvent this issue, Bertozzi added two fluorines adjacent to the internal acetylene. The new difluorinated cyclooctyne (DIFO) reacts with azides at a rate comparable to the standard copper catalyzed cycloaddition.

Another approach to enhancing the reactivities of cyclooctynes is by building strains into the cyclooctyne rings. For example, a cyclooctyne flanked by two benzene rings was designed, in which the aromaticity of the benzenes increases the ring strain. In yet another approach, the cyclooctyne ring may be activated by fusing a small ring with the cyclooctyne ring. All these cyclooctynes will be referred to generally as "activated" cyclooctynes, whether they are activated by aromatic rings, fluorines, or ring strains.

In accordance with embodiments of the invention, both Cu(I)-catalyzed and Cu(I)-free "click" reactions may be used. The conditions of these reactions are well known to one skilled in the art, see e.g., the discussion above.

In accordance with embodiments of the invention, reagents that can participate in "click" reactions may be used in the oligonucleotide synthesis to facilitate the purification of the polynucleotide products. Such reagents may include a terminal alkyne or an activated cyclooctyne moiety. An activated cyclooctyne moiety may include those activated by having flanking aromatic rings, having fluorine substitutions next to the triple bond, or having a ring strain (e.g., cyclopropane rings fused with cyclooctyne rings).

In accordance with embodiments of the invention both terminal alkynes and activated cyclooctynes may be used. The terminal alkynes and the activated cyclooctynes are generally referred to as "click handles" herein. Thus, a generic formula of a reagent of the invention may be represented as:

  Formula (A)

wherein

X is a functional group that can react with the 5'-hydroxyl group on a nucleoside, nucleotide, oligonucleotide, or the like; Suitable X functional groups may include phosphoramidite, H-phosphonate, acetal, isocyanate, etc C is a direct bond or a cleavable adaptor wherein the cleavable adaptor is represented by —$C_a$—$C_b$—, wherein $C_a$ is connected to X and is a direct bond, hydrocarbyl, aryl, heteroaryl, cycloalkyl, heterocyclyl, a nucleoside, each of which is optionally substituted with one to two substituents selected from halo, hydroxyl, ($C_1$-$C_6$) alkoxy, ($C_1$-$C_6$) alkyl, amino or alklyamino; $C_b$ is a direct bond, a silanyl group, a trityl group, or a vicinyl alcohol group. Preferably $C_a$ is a direct bond, ($C_1$-$C_{12}$)hydrocarbyl, ($C_6$-$C_{12}$)aryl, 5- to 12-membered heteroaryl, ($C_3$-$C_{12}$)cycloalkyl, 4- to 12-membered heterocyclyl, or a nucleoside;

L is a hydrocarbyl chain which may be optionally substituted with one to four substituent groups independently selected from the group consisting of 5-to 9-membered heteroaryl, 4- to 9-membered heterocyclyl, amino, ether, carboxyl, carbamoyl, ($C_6$-$C_{12}$)aryl, —O—R", —O—CO—R", —NR'—R", —NR'—CO—R", —CO—NR'—R", —CO—R", —CN, halogen, or a combination thereof, wherein R' and R" are independently H or ($C_1$-$C_6$)hydrocarbyl; Preferably L is hydrocarbyl such as ($C_1$-$C_{12}$)alkyl, ($C_2$-$C_{12}$)alkenyl, or ($C_2$-$C_{12}$)alkynyl, each of which may be optionally substituted with one to two substituent groups selected from amino, ether, carboxyl, carbamoyl, or halogen;

Or L may be a hydrocarbyl chain interspersed with other atoms, as represented by —(CHR')$_a$—W$_b$—(CHR')$_c$—V$_d$—(CHR')$_e$—, wherein W and V are independently —O—, —S—, or —NR'—; R' is H or ($C_1$-$C_6$)alkyl; and a, b, c, d, and e are independently an integer from 0 to 10, preferably from 0 to 6, or preferably from 0 to 3, and the sum of a, b, c, d, and e is preferably an integer from 2 to 6.

H is a "click handle," as defined above and may include a terminal alkyne or an activated cyclooctyne.

A particular example of a compound with a phosphoramidite, a linker, and a "click handle" is shown below. In this example, "C" in formula (A) is a direct bond.

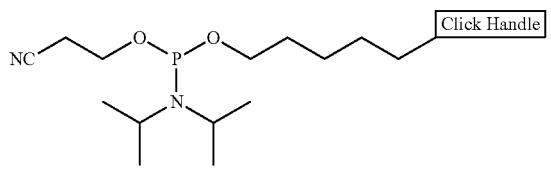 [SMILES: CCCCCCOP(OCCC#N)N(C(C)C)C(C)C]

In the above formula, the "click handle" may be a terminal alkyne or an activated cyclooctyne. An example of a terminal alkyne reagent and an example of a generic "activated cyclooctyne" reagent are illustrated below. As noted above, the "activated cyclooctyne" may be activated by aromatic rings, fluorines, or fused ring strains.

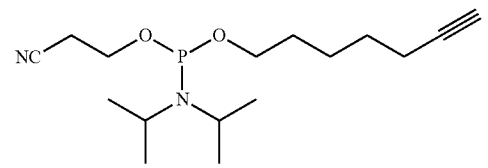

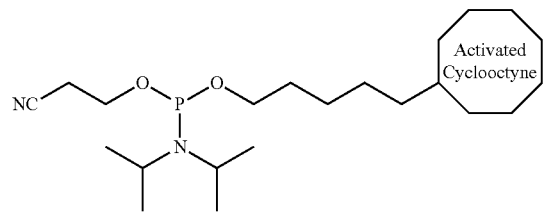

While reagents containing both terminal alkynes and activated cyclooctynes may be used, for clarity, the following description may use activated cyclooctynes as examples. Particularly, the following description will use fused ring cyclooctynes (i.e., strained cyclooctynes) as examples. These "strained" cyclooctynes may be referred to generally as "activated" cyclooctynes in the following description. However, one skilled in the art would appreciate that the description also applies to terminal alkyne-containing reagents or other types of activated cyclooctyne reagents.

Reagents of the invention having an activated cyclooctyne may be represented as a general structure shown as Formula (B):

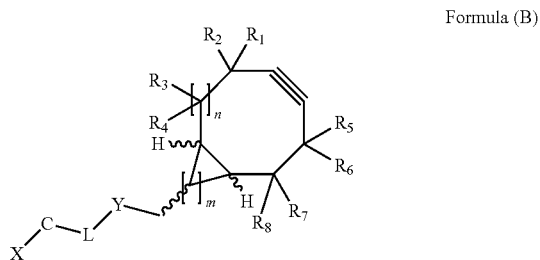

Formula (B)

wherein m, n are each independently an integer selected from 0 to 10; $R_1$-$R_8$ are are each independently selected from H, halo, nitro, ester, carboxylic acid, aldehyde, ether, or cyanoethyl, an electron withdrawing group, an electron donating group, N(R')(R''), alkyl, alkenyl, aryl, heteroaryl, cycloalkyl, heterocyclyl, bicyclyl, CO—NR'R'', O-hydroxyalkyl, O-hydroxyalkenyl, CO-alkoxyalkenyl, wherein R' and R'' are each H or a lower alkyl (e.g., ($C_1$-$C_6$)alkyl); X, C and L are defined in Formula (A) and Y is a linkage functional group selected from —O—, —S—, —NR'—, —NH—CO—O—, —O—CO—NH—, —NH—CO—NH—, wherein R' is hydrogen or a lower alkyl (e.g., ($C_1$-$C_3$)alkyl or ($C_1$-$C_6$) alkyl).

An exemplary reagent of a compound of Formula (B) with a strained cyclooctyne is shown in Formula (I):

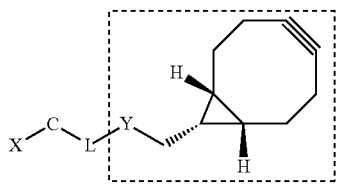

Formula (I)

wherein the moiety enclosed by the dotted box corresponds to H in formula (A), wherein Y is a linkage functional group selected from —O—, —S—, —NR'—, —NH—CO—O—, —O—CO—NH—, —NH—CO—NH—, wherein R' is hydrogen or a lower alkyl (e.g., ($C_1$-$C_3$)alkyl or ($C_1$-$C_6$) alkyl); X, C and L are defined above in Formula (A).

In accordance with some embodiments of the invention, X may include a phosphoramidite group, an H-phosphonate group, an acetal group, or an isocyanate group. Specific examples of X may include acetal (e.g., —CH(OR)$_2$), isocyanate (—N=C=O), (2-cyanoethyl)-diisoproylphosphoramidite (NC—(CH$_2$)$_2$—O—PO—N(iPr)$_2$), and methyl-diisoproylphosphoramidite, H-phosphonate alkyl esters and the like.

In accordance with some embodiments of the invention, C is the cleavable adaptor represented by —$C_a$—$C_b$—, wherein $C_a$ is connected to X and is a direct bond, ($C_1$-$C_{12}$)hydrocarbyl, ($C_6$-$C_{12}$)aryl, 5- to 12-membered heteroaryl, ($C_3$-$C_{12}$) cycloalkyl, 4- to 12-membered heterocyclyl, a nucleoside, each of which is optionally substituted with one to two substituents selected from halo, hydroxyl, ($C_1$-$C_6$) alkoxy, ($C_1$-$C_6$) alkyl, amino or alklyamino; $C_b$ is a direct bond, a silanyl group, a trityl group, or a vicinyl alcohol group. Preferably $C_a$ is a direct bond, ($C_1$-$C_6$)hydrocarbyl, 4- to 12-membered heterocyclyl, or nucleoside; $C_b$ is a direct bond, a silanyl group, or a trityl group.

In accordance with some embodiments of the invention, L may be represented by a generic formula of —(CH$_2$)$_a$—$W_b$—(CH$_2$)$_c$—$V_d$—(CH$_2$)$_e$—, wherein W and V are independently —O—, —S—, or —NR'—, wherein R' is hydrogen or a lower alkyl (e.g., ($C_1$-$C_3$)alkyl or ($C_1$-$C_6$)alkyl); and a, b, c, d, and e are independently an integer from 0 to 10, preferably from 0 to 6, or preferably from 0 to 3, and the sum of a, b, c, d, and e is preferably an integer from 2 to 6.

In accordance with some embodiments of the invention, L is a hydrocarbyl group such as ($C_1$-$C_{12}$)alkyl, ($C_2$-$C_{12}$)alkenyl, or ($C_2$-$C_{12}$)alkynyl, each of which may be optionally substituted with a group selected from amino, ether, carboxyl, carbamoyl, or halogen. In accordance with some embodiments of the invention, the L linker is preferably ($C_1$-$C_{12}$) alkyl, more preferably ($C_1$-$C_6$)alkyl.

In accordance with some embodiments of the invention, the X in Formula (I) is a phosphoramidite. Examples of such compounds may have a general structure shown in Formula (II):

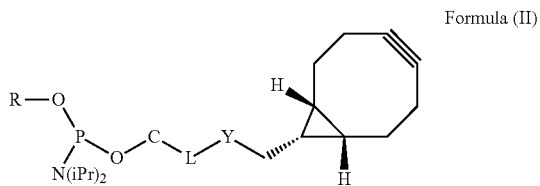

Formula (II)

wherein C, L and Y are as defined above and R is $(C_1\text{-}C_6)$alkyl or cyanoethyl. In preferred embodiments of the invention, L is $(C_1\text{-}C_{12})$alkyl, or more preferably $(C_1\text{-}C_6)$alkyl, and Y is —NH—CO—O—, C is the cleavable adaptor represented by —$C_a$—$C_b$—, wherein $C_a$ is connected to X and is a direct bond, $(C_1\text{-}C_6)$hydrocarbyl, 4- to 12-membered heterocyclyl, or nucleoside; $C_b$ is a direct bond, a silanyl group, or a trityl group, and R is cyanoethyl.

In accordance with some embodiments of the invention, the X in Formula (I) is an H-phosphonate. Examples of such compounds may have a general structure shown in Formula (III):

Formula (III)

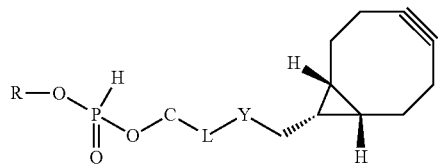

wherein C, L, Y and R are as defined above. In preferred embodiments of the invention, L is $(C_1\text{-}C_{12})$alkyl, or more preferably $(C_1\text{-}C_6)$alkyl, Y is —NH—CO—O—, C is the cleavable adaptor represented by —$C_a$—$C_b$—, wherein $C_a$ is connected to X and is a direct bond, $(C_1\text{-}C_6)$hydrocarbyl, 4- to 12-membered heterocyclyl, or nucleoside; $C_b$ is a direct bond, a silanyl group, or a trityl group, and R is cyanoethyl In accordance with some embodiments of the invention, the X in Formula (I) is an isocyanate. Examples of such compounds may have a general structure shown in Formula (IV):

Formula (IV)

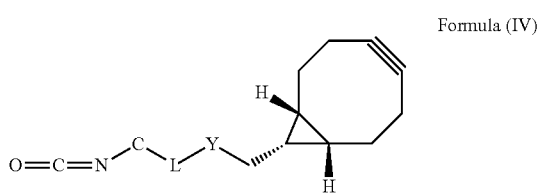

wherein L, C and Y are as defined above. In preferred embodiments of the invention, L is $(C_1\text{-}C_{12})$alkyl, or more preferably $(C_1\text{-}C_6)$alkyl, Y is —NH—CO—O—, and C is the cleavable adaptor represented by —$C_a$—$C_b$—, wherein $C_a$ is connected to X and is a direct bond, $(C_1\text{-}C_6)$hydrocarbyl, 4- to 12-membered heterocyclyl, or nucleoside; $C_b$ is a direct bond, a silanyl group, or a trityl group.

Some representative examples of compounds of Formula (II) are shown below. One skilled in the art would appreciate that these specific compounds are for illustration only and other modifications and variations of these compounds are possible without departing from the scope of the invention.

(Compound 1)

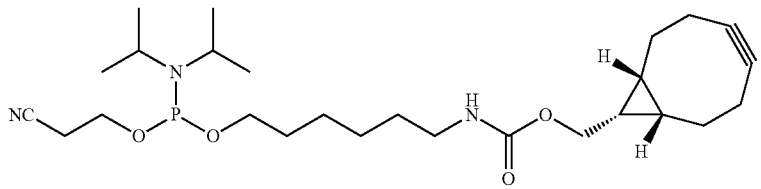

(Compound 2)

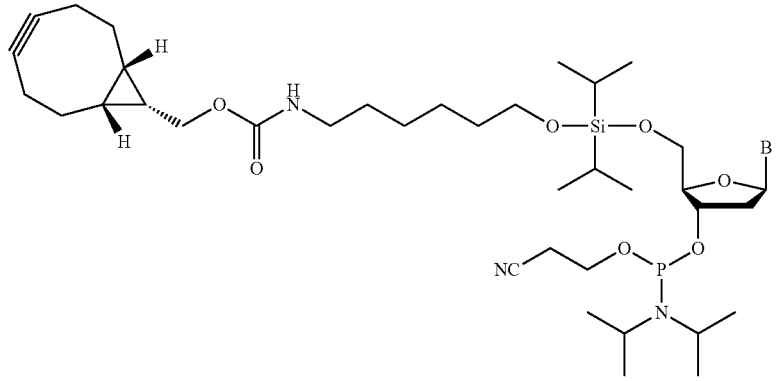

(Compound 3)

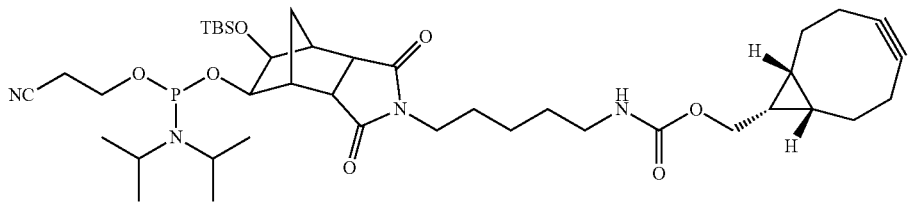

-continued

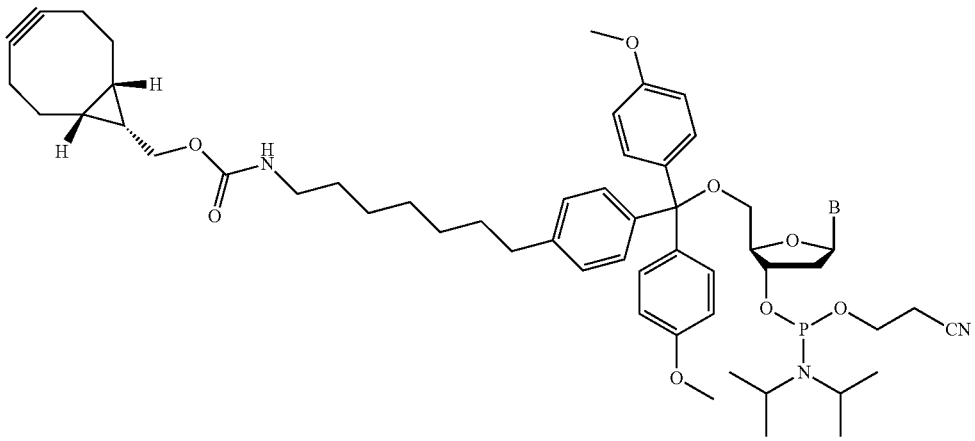

(Compound 4)

Compound 1 is a phosphoramidite, which can react with a hydroxyl group to form a phosphite group. The phosphite group may be oxidized to a phosphate group, e.g., during the oxidation step in a typical oligonucleotide synthesis. The phosphate group is stable to the iterative couplings and deprotections used in the synthesis of an oligonucleotide. In addition, the phosphate group is stable to the final deprotection and cleavage of a polynucleotide from the solid support. Therefore, activated cyclooctyne reagents having a structure like compound 1 can be used as capping agents to tag the failure sequences to facilitate the purification of polynucleotides after synthesis, as described below.

Although not shown, an H-phosphonate (instead of phosphoramidite) may also be used. An H-phosphonate can react with a hydroxyl group to form a phosphonate group. The phosphonate group is stable to the iterative couplings and deprotections used in the synthesis of an oligonucleotide. The phosphonate group may be oxidized to a phosphate group, e.g., during the oxidation step in a typical oligonucleotide synthesis. The phosphate group is stable to the final deprotection and cleavage of a polynucleotide from the solid support. Therefore, activated cyclooctyne reagents having a structure like compound 1, but having an H-phosphonate instead of a phosphoramidite, can be used as capping agents to tag the failure sequences to facilitate the purification of polynucleotides after synthesis, as described below.

Compound 2 is a nucleoside 3'-phosphoramidite having an activated cyclooctyne moiety linked to the 5'-hydroxyl group. The 3'-phosphoramidate group on this reagent can react with a 5'-hydroxyl group to form a phosphite group. The phosphite group may be oxidized to a phosphate group, e.g., during the oxidation step in a typical oligonucleotide synthesis. The phosphate group is stable to the iterative couplings and deprotections used in the synthesis of an oligonucleotide. In addition, the phosphate group is stable to the final deprotection and cleavage of a polynucleotide from the solid support.

The activated cyclooctyne moiety in compound 2 is linked to the nucleoside via a silanyl group, which may be cleaved upon treatment with a mild acid solution or fluoride ion (e.g., NaF, tetra-N-butylammonium fluoride ((Bu)$_4$NF), HF-pyridine or HF-NEt$_3$). Therefore, the activated cyclooctyne moieties may be released from the polynucleotide products after serving their functions to facilitate the purification of the final polynucleotides. Accordingly, reagents having a structure like compound 2 can be used as a last nucleoside to couple to the growing chain of the desired sequence.

After synthesis, the full length sequence can be separated from failure sequences via a "click" reaction to capture the full length sequence on an azide or nitrone-containing solid support, as described below. After purification of the full length sequence, the activated cyclooctyne moiety can be severed by treating the product with a mild acid solution or fluoride ion (e.g., NaF, tetra-N-butylammonium fluoride ((Bu)$_4$NF), HF-pyridine or HF-NEt$_3$), and the desired full length sequence may be isolated.

Compound 3 is similar to compound 1 in that an activated cyclooctyne is lined to a phosphoramidite. However, the linker portion of Compound 3 includes a norboranyl group that has vicinal alcohols, one of which is bonded to the phosphoramidite and the other alcohol is protected with a TBS (t-butyldimethylsilyl) group. This may serve as a universal-type "click" handle (i.e., for use to cap the failure sequences or for use to couple to the last nucleotide in the synthesis cycle). The TBS protection group may be removed by treatment with a mild acid solution or fluoride ion (e.g., NaF, tetra-N-butylammonium fluoride ((Bu)$_4$NF), HF-pyridine or HF-NEt$_3$). Once the hydroxyl is freed, it can attack the neighboring phosphate group with heating or basic treatment such as ammonia. Thus, the activated cyclooctyne group in Compound 3 can function as a releasable "click" handle, which can be released when it has served its function to facilitate the purification of the desired sequences.

As in Compound 1, the phosphoramidite group in Compound 3 can react with a hydroxyl group to form a phosphite group. The phosphite group may be oxidized to a phosphate group, e.g., during the oxidation step in a typical oligonucleotide synthesis. The phosphate group is stable to the iterative couplings and deprotections used in the synthesis of an oligonucleotide. In addition, the phosphate group is stable to the final deprotection and cleavage of a polynucleotide from the solid support. Therefore, activated cyclooctyne reagents having a structure like compound 1 can be used as capping agents to tag the failure sequences to facilitate the purification of polynucleotides after synthesis, as described below.

In addition, because the "click" handle is releasable, Compound 3 may also be used as a temporary capping agent after the last nucleotide has been added, instead of using Compound 3 as capping agents for the failure sequences.

Instead of a cleavable silanyl group, a trityl group may also be used as a cleavable connector. The trityl connector can be removed by treatment with a mild acid, such as dichloroacetic acid or trifluoroacetic acid. An example of a compound that uses a trityl connector is shown as Compound 4. While both silanyl and trityl groups are shown with one example, one skilled in the art would appreciate that various modifications and variations are possible without departing from the scope of the invention.

As noted above, the activated cyclooctyne reagent in accordance with embodiments of the invention may be used as "click" chemistry handles in the synthesis and purification of oligonucleotides. These reagents can be used in two approaches: (i) as "capping" agents to block the failure sequences from further reacting in the subsequent reactions, and (ii) as last nucleotide analogs to label the final products for easier purification.

In the first approach according to embodiments of the invention, short-mers (truncated oligonucleotides), which are generated as a result of incomplete coupling during iterative oligonucleotide synthesis, are "capped-off" with a novel activated cyclooctyne phosphorylating reagent. Exemplary processes for using the strained cyclooctyne reagents in the synthesis and purification of oligonucleotides according to methods of the invention are illustrated in FIGS. 2 and 4.

Figure 2:
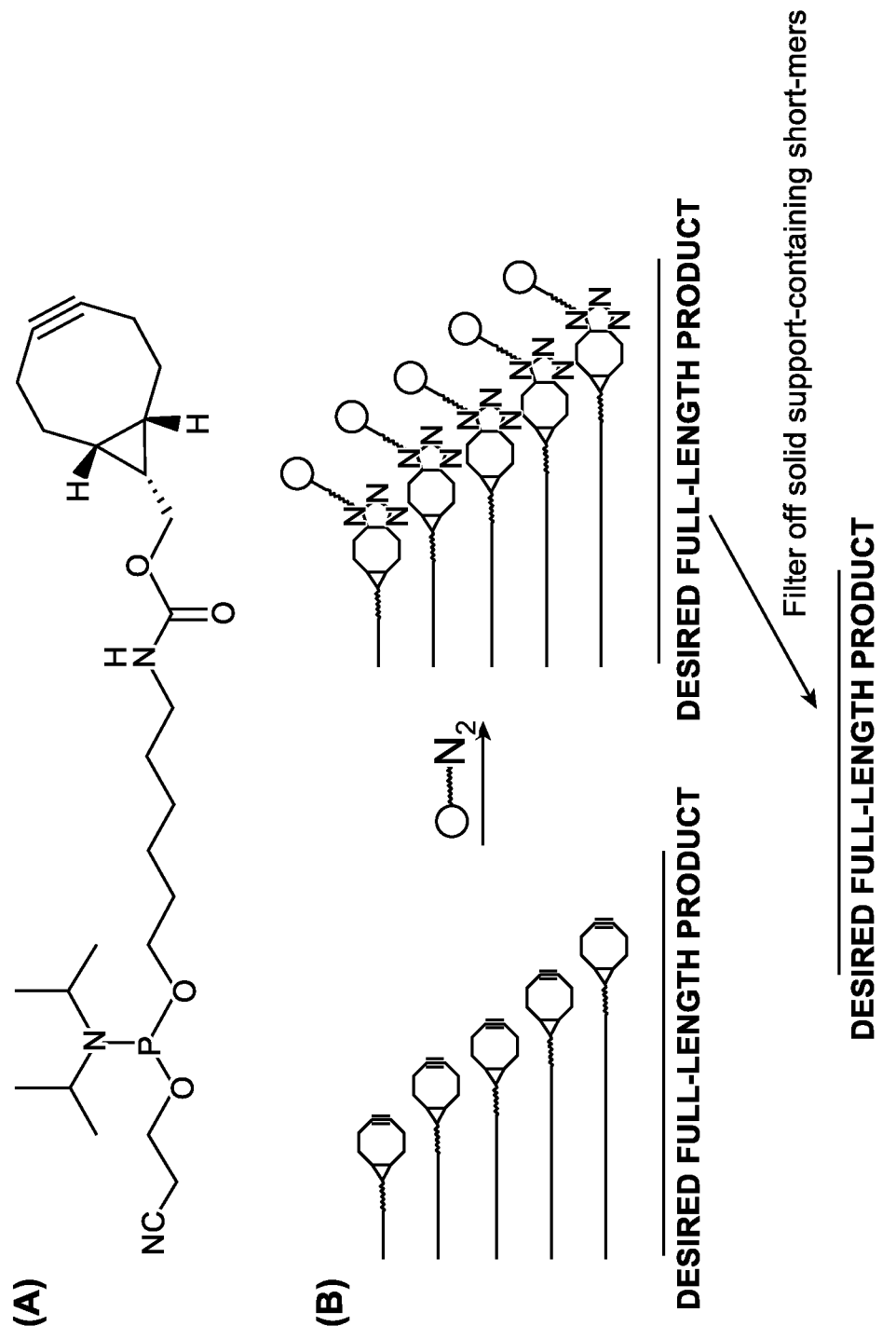
FIG. 2 panel A shows an activated cyclooctyne reagent in accordance with one embodiment of the invention.
Figure 4:
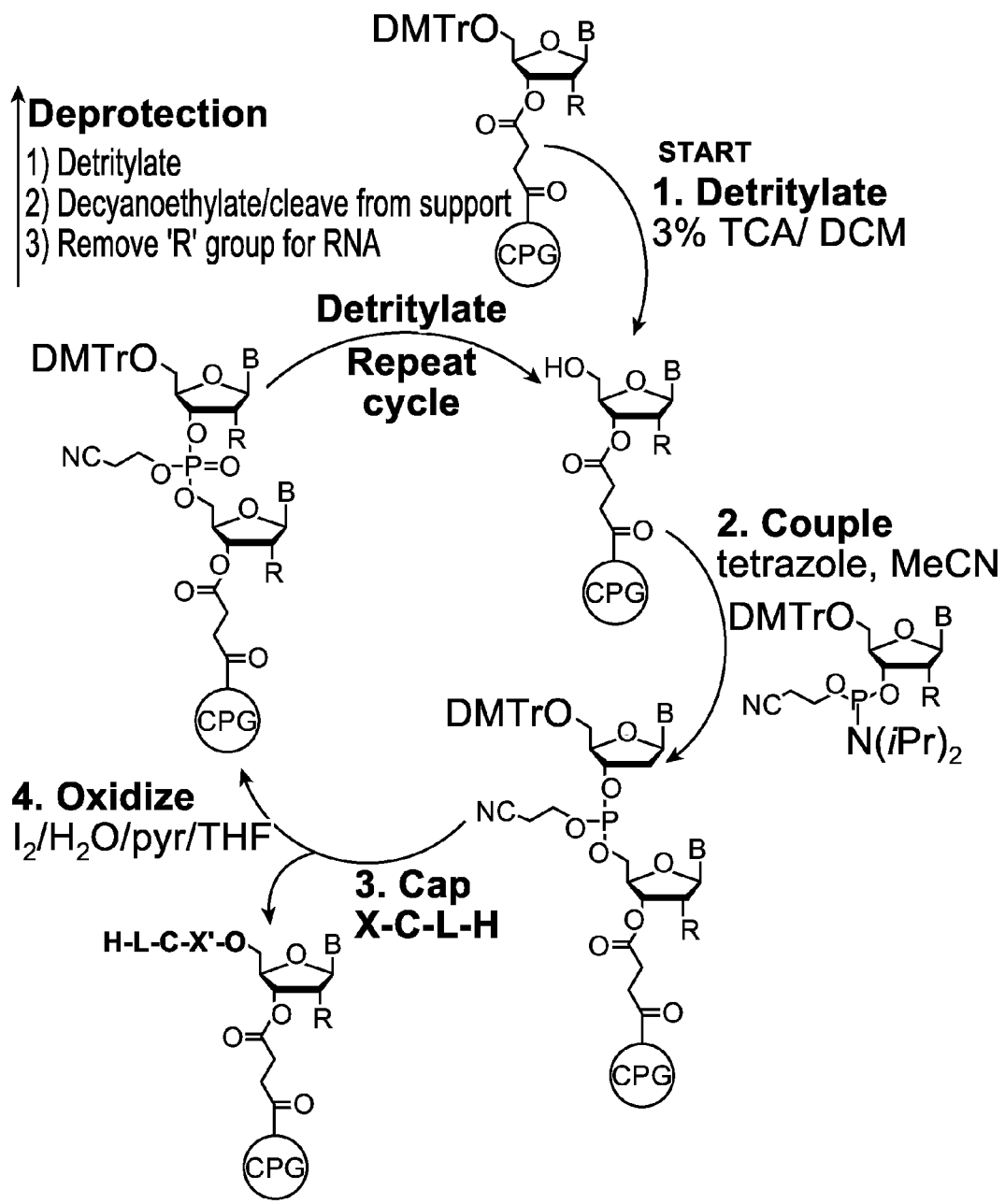
FIG. 4 shows a schematic illustrating an oligonucleotide synthesis cycle using a terminal alkyne or an activated cyclooctyne reagent as a capping agent in accordance with one embodiment of the invention.

Referring to FIGS. 2 and 4, in each synthetic cycle, the capping step may be modifies to use a strained cyclooctyne reagent of the invention (e.g., Compound 1 or Compound 3 shown above). That is, the acetic anhydride (i.e., $Ac_2O$) may be replaced with a reagent of the invention, i.e., X—C—L—H (e.g., Compound 1 or Compound 3) in step 3 in FIG. 4. As a result of these capping reactions, the final product mixture after cleavage from the solid support would include, in addition to the full sequence, various failure sequences each with an activated cyclooctyne moiety attached to the 5'-end (see FIG. 2).

The product mixture may be reacted with azide-containing or nitrone-containing solid support (e.g., beads). Nitrones are an N-oxides of imines. Azides and nitrone can react readily with alkynes to form stable 5-membered ring products. After the cycloaddition, the failure sequences will be covalently attached to the solid support, while the full length sequence will remain in solution. Therefore, the desired full length sequence can be readily separated from the failure sequences, e.g., by filtration.

In the second approach, a novel cleavable activated-cyclooctyne phosphorylating reagent may be added to the 5'-end of the oligonucleotide (during the final step of iterative synthesis) as a purification handle of the final full-length product itself. Alternatively, the final monomer to be coupled may include a cleavable activated cyclooctyne moiety. Examples of cleavable activated-cyclooctyne phosphorylating reagents may include Compound 2, Compound 3, or Compound 4 (shown above).

Figure 3:
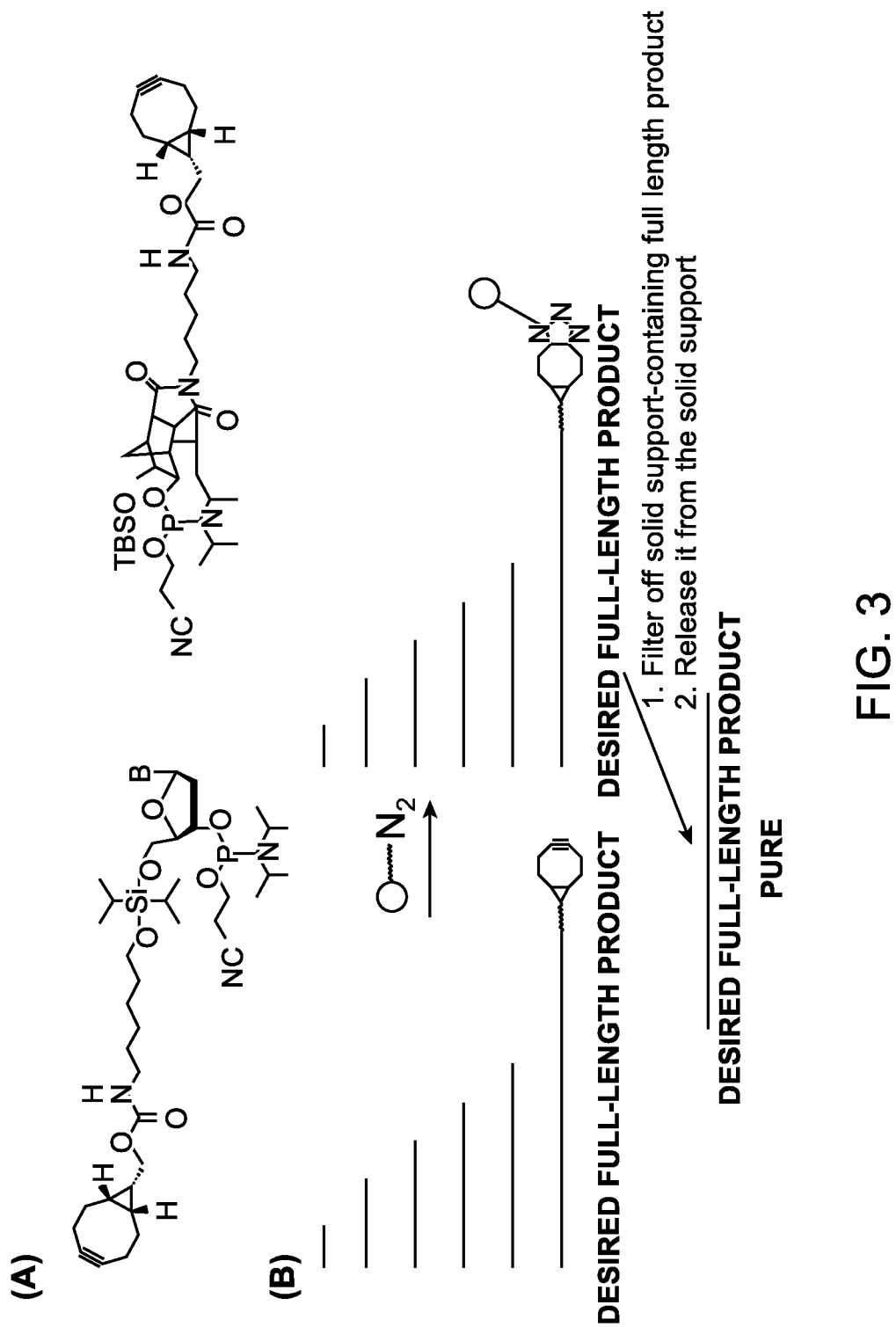
FIG. 3 panel A shows two activated cyclooctyne reagents in accordance with some embodiments of the invention.
Figure 5:
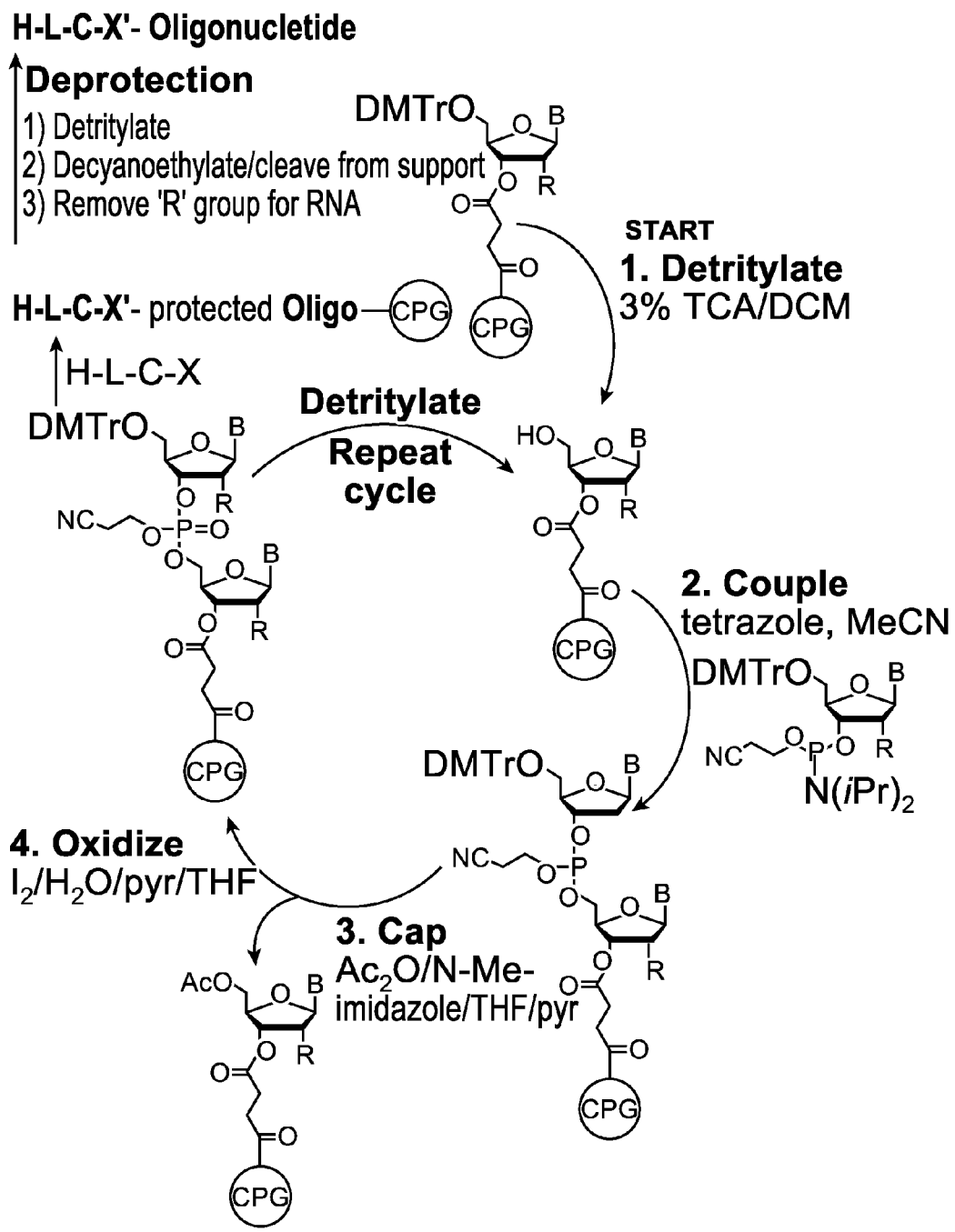
FIG. 5 shows a schematic illustrating an oligonucleotide synthesis cycle using a terminal alkyne or an activated cyclooctyne reagent as a last nucleotide or as a terminal 5'-hydroxyl group protecting agent in accordance with one embodiment of the invention.

A method in accordance with this approach is illustrated in FIGS. 3 and 5. As shown in FIGS. 3 and 5, the final product mixture contains various failure sequences that are not tagged with the activated cyclooctyne reagents, whereas the full length product is covalently linked to an activated cyclooctyne group.

The product mixture may be reacted with azide-containing or nitrone-containing solid support (e.g., beads) to form covalent bonds with the full length oligonucleotide product. The failure sequences, which remain in solution, can be separated from the solid support. The purified full length product attached to the solid support can then be released by cleaving the oligonucleotide from the beads, such as using a mild acid solution or fluoride ion (e.g., NaF, tetra-N-butylammonium fluoride ($(Bu)_4NF$), HF-pyridine or HF-$NEt_3$).

The use of activated cyclooctyne phosphorylating reagents to cap and trap failure sequences or the use of activated cyclooctyne phosphoramidite monomers or similar reagents at the end of the oligonucleotide cycles will greatly improve synthesis and ease of purification. These methods will allow for rapid purification of oligonucleotides both in a high throughput and large scale settings. These straightforward methods will also cut down the costs of oligonucleotide synthesis/purification. It will also increase the overall yields and recoveries of desired full-length products. It will be most powerful in the purification of long oligonucleotides, i.e., 300+-mers) where all of the conventional methods fail. However, these methods are also advantageous over the prior art methods for shorter oligonucleotides.

Embodiments of the invention will be further illustrated with examples below. It should be noted that these examples are for illustration only and not meant to limit the scope of the invention.

EXAMPLES

Embodiments of the invention will be illustrated with the following examples. These examples are for illustration only and are not meant to limit the scope of the invention. Furthermore, one skilled in the art would appreciate that various variations and modifications are possible from these examples without departing from the scope of the invention. For example, the linkers used may be substituted with another linker with longer or shorter linkage or with a different types of linker. Similarly, while these examples use phosphoramidite functional groups, one skilled in the art would appreciate that similar reagents may be prepared with an H-phosphonate moiety, using procedures known in the art.

Scheme 1, shown below, illustrates a synthetic scheme for the synthesis of an analog of compound 1 described above. Briefly, 1,5-cyclooctadiene is reacted with a diazo acetate to form a fused cyclopropyl-cyclooctene structure 3476-31, the ester functional group of which is reduced to the corresponding alcohol. Then, the cyclooctene moiety is brominated and dehydrobrominated to produce the corresponding fused cyclopropyl-cyclooctyne alcohol 3476-39.

The alcohol functional group of the fused cyclopropyl-cyclooctyne alcohol 3476-39 is converted to a carbonate containing a p-nitrophenol group. The p-nitrophenol group in the carbonate can be displaced with a nucleophile, such as an amine. Therefore, a desired linker containing an amino group can be reacted with the carbonate compound to produce a activated cyclooctyne coupled to a linker via a carbamate functional group (—O—C(O)—NH—), e.g., 3476-105. Finally, the other end of the linker may be converted into phosphoramidites or H-phosphonates, which can be used in oligonucleotide synthesis procedures.

Scheme 1. Synthesis of Activated cyclooctyne phosphoramidite moiety

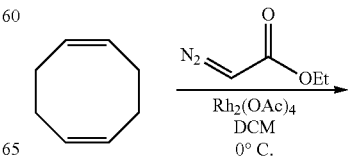

-continued

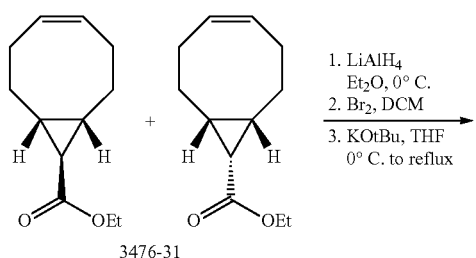

3476-31

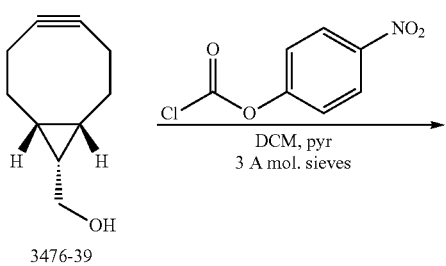

3476-39

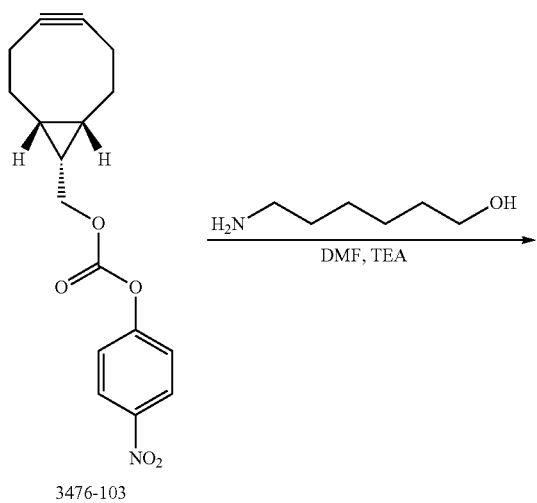

3476-103

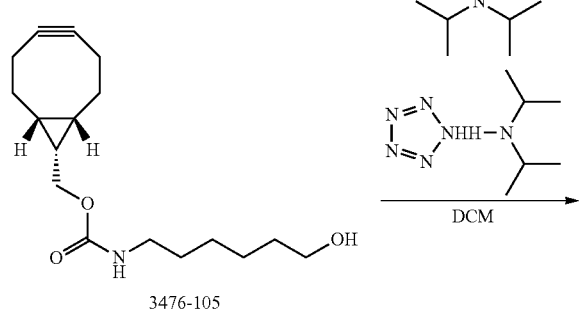

3476-105

-continued

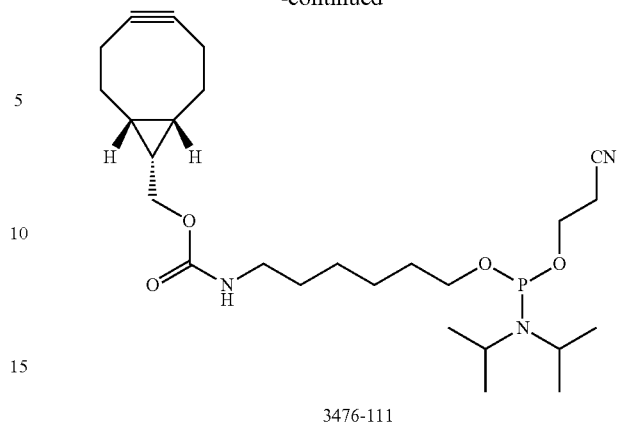

3476-111

In Scheme 1, only one of the two stereoisomers of compound 3476-31 is shown in the subsequent steps. This is for clarity of illustration. One may use a racemic mixture or the other isomer instead.

Furthermore, scheme 1 illustrates that a linker is coupled to an activated cyclooctyne group via a carbamate functional group, i.e., —O—C(O)—NH—$(CH_2)_6$—O—. One skilled in the art would appreciate that other types of linkage functional group (e.g., ether, ester, etc.) may be used without departing from the scope of the invention. Preparation of such other linkage functional group would involve common organic reactions and one skilled in the art would not have any difficulty in preparing these compounds. As an example, an ether linkage, for example, may be prepared according to the following reaction scheme:

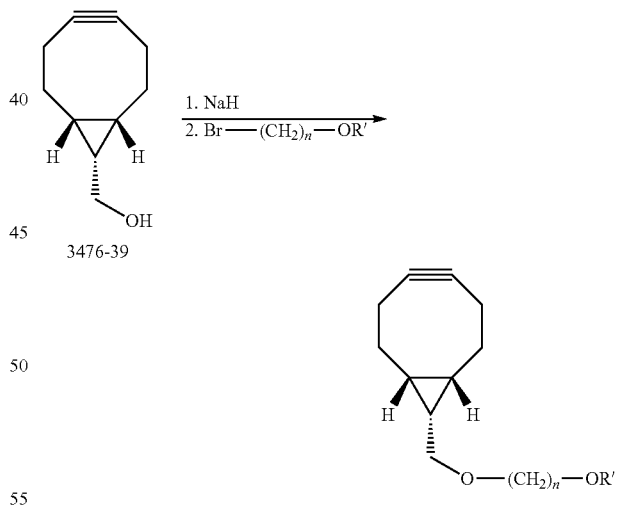

In accordance with embodiments of the invention, the lengths of the linkers may be varied. For example, in —$(CH_2)_n$—, n may be an integer in the range of 2-10. In addition, the alcohol group in compound 3476-39 may be converted into an amino group or a leaving group (e.g., tosylate), which can then be further reacted to provide different types of linkage functional groups.

In accordance with embodiments of the invention, various linkage functional groups and various linkers may be used. Some of these examples are discussed as the Y and L group, with reference to Formula I above.

One may generalize the "—Y-L-" portion of the molecule as a "linker box," as shown in Formula (V) below.

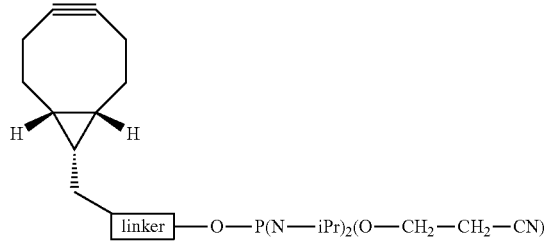

Formula (V)

Non-exhaustive examples of such "linker boxes" (see Formula (V)) may include: —NH—(CH$_2$)$_2$—, —NH—(CH$_2$)$_3$—, —NH—(CH$_2$)$_4$—, —NH—(CH$_2$)$_5$—, —NH—(CH$_2$)$_6$—, —O—(CH$_2$)$_2$—, —O—(CH$_2$)$_3$—, —O—(CH$_2$)$_4$—, —O—(CH$_2$)$_5$—, —O—(CH$_2$)$_6$—, —NH—(CH$_2$)$_2$—, —NH—(CH$_2$)$_3$—, —NH—(CH$_2$)$_4$—, —NH—(CH$_2$)$_5$—, —NH—(CH$_2$)$_6$—, —NH—CO—(CH$_2$)$_2$—, —NH—CO—(CH$_2$)$_3$—, —NH—CO—(CH$_2$)$_4$—, —NH—CO—(CH$_2$)$_5$—, —NH—CO—(CH$_2$)$_6$—, —NH—CO—O—(CH$_2$)$_2$—, —NH—CO—O—(CH$_2$)$_3$—, —NH—CO—O—(CH$_2$)$_4$—, —NH—CO—O—(CH$_2$)$_5$—, —NH—CO—O—(CH$_2$)$_6$—, —O—(CH$_2$)$_2$—O—(CH$_2$)$_2$—, —O—(CH$_2$)$_3$—O—(CH$_2$)$_2$—, —NH—(CH$_2$)$_2$—O—(CH$_2$)$_2$—, —NH—(CH$_2$)$_3$—O—(CH$_2$)$_2$—, —NH—CO—(CH$_2$)$_2$—O—(CH$_2$)$_2$—, —NH—CO—(CH$_2$)$_3$—O—(CH$_2$)$_2$—, etc.

As shown in Scheme 1, the reactions involved are common organic reactions. One of ordinary skill in the art would be able to carry out these reactions without inventive efforts. As an example, detailed synthetic procedures and conditions for the synthesis of an exemplary activated cyclooctyne phosphoramidite moiety 3476-31 will be described below.

Synthesis of Compound 3476-31

To a solution of 1,5-cyclooctadiene (51.57 mL, 0.420 mol) and Rh$_2$(OAc)$_4$ (1 g, 0.0026 mol) in DCM (30 mL), an 82% solution of ethyl diazoacetate (7.32 mL in DCM, 0.0605 mol) was added drop wise over 3 h at 0° C. This solution was stirred for 48 h. It was then evaporated to dryness. Excess cyclooctadiene was removed by filtering through a pad of silica using 1:200 EtOAc/hexanes (1 L). The filtrate was concentrated in vacuo and the residue was purified using column chromatography on silica gel (1:20 EtOAc/hexanes) giving a clear colorless oil. The endo compound has a higher Rf than the exo compound. Compound conforms as described by Dommerholdt, Angew. Chem. Int. Ed. 2010, 49, 9422.

Synthesis of Compound 3476-39

A suspension of LiAlH$_4$ (334 mg, 88 mmol) in diethyl ether (100 mL) was cooled to 0° C. This was followed by the drop wise addition of 3476-31 (1.7 g, 88 mmol) in ether (50 mL). The mixture was then stirred for 30 min at room temp, then cooled to 0° C., and water was slowly added until the grey solid had turned white. Sodium sulfate was then added and the solid was filtered off and washed with ether, and the filtrate was concentrated in vacuo. It was then dissolved in DCM (200 mL) and cooled to 0° C. A solution of bromine (0.5 mL, 97 mmol) was then added drop wise in DCM (20 mL) until the yellowish color persisted. The reaction mixture was then stirred for an additional 30 min. At this point it was quenched with a 10% aqueous sodium thiosulfate solution (50 mL) and extracted with DCM. The organic layer was dried over sodium sulfate, filtered, and concentrated in vacuo to afford the dibromide as a yellowish oil. This material was then dissolved in THF (50 mL) followed by the addition of a solution of potassium tert-butoxide (3 g, 264 mmol) in THF (15 mL) at 0° C. The solution was then refluxed for 3 h. After cooling to room temperature, the reaction mixture was diluted with DCM (200 mL) and quenched with saturated ammonium chloride solution (50 mL). The organic layer was dried over sodium sulfated, filtered, and evaporated, and filtered in vacuo. The yellowish residue was then purified by column chromatography using 7:3 hexanes/EtOAc giving a white solid. Compound conforms as described by Dommerholdt, Angew. Chem. Int. Ed. 2010, 49, 9422.

Synthesis of Compound 3476-103

Compound 3476-39 (1.84 g, 0.0122 mol) was dissolved in DCM (25 mL) under nitrogen. This was followed by the addition of pyridine (5 mL) and 3 Å molecular sieves. The solution was then stirred for 15 min at room temperature. This was followed by the addition of p-Nitro phenyl chloroformate (3.2 g, 0.0159 mol). The reaction was stirred until completion (2 h) as judged by TLC (using 7/3 hexanes:EtOAc). Upon completion, the reaction was diluted with DCM and worked up with aqueous 5% ammonium chloride. The organic layer was dried over sodium sulfate, filtered, and evaporated in vacuo. The resulting material was then purified by column chromatography using 7:3 hexanes/EtOAc giving a white solid. Compound conforms as described by Dommerholdt, Angew. Chem. Int. Ed. 2010, 49, 9422.

Synthesis of Compound 3476-105

Compound 3476-103 (2.47 g, 0.00784 mol) was dissolved in DMF (25 mL) under nitrogen. This was followed by the addition of triethylamine (3.3 ml, 0.0235 mol) and aminohexanol (1.84 g, 0.157 mol). The reaction mixture was complete after 1 h. At this point it was evaporated to dryness and redissolved in DCM (200 mL). The organic layer was then washed with 1 N NaOH (2×50 mL), and sat. ammonium chloride. The organic layer was then dried over sodium sulfate, filtered and evaporated in vacuo. The resulting material was then purified by column chromatography using a gradient up to 5% MeOH in DCM giving a white solid in 94% yield. $^1$H NMR (500 MHz, CDCl$_3$) δ 4.72 (1H), 3.94 (2H, d), 3.60 (2H, t), 3.14-3.15 (2H, m), 2.37 (2H, d), 2.23-2.28 (2H, m), 2.10-2.14 (2H, m), 1.80 (1H, s), 1.45-1.57 (4H, m), 1.33-1.34 (6H, m), 0.71-0.73 (2H, s), 0.63-0.66 (1H, m); $^{13}$C NMR (126 MHz, CDCl$_3$) δ 156.84, 98.77, 68.90, 62.60, 40.75, 33.27, 32.54, 29.97, 26.35, 25.29, 23.75, 22.79, 21.36; ESI-QQQ calc. for C$_{17}$H$_{27}$NO$_3$ 293.2 (+H$^+$); found 294.2.

Synthesis of Compound 3476-111

Compound 3476-105 (500 mg, 17 mmol) and diisopropyltetrazolide (586 mg, 0.00241 mmol) were added to a round bottom flask that contained 3 Å molecular sieves under dry nitrogen. This was followed by the addition of DCM (5 mL). This material was then allowed to stir for 30 min at room temp at which point the phosphitylating reagent (388 mg, 13 mmol), dissolved in DCM (5 mL), was cannulated into the round bottom flask. This reaction was allowed to proceed until completion as judged by TLC (3% MeOH in DCM). It was then quenched with 5% sodium bicarbonate and extracted with DCM. The organic layer was dried over sodium sulfate, filtered, and evaporated in vacuo. The residual material was then purified by column chromatography using 3:7 hexanes/EtOAc with 1% TEA to give a clear colorless oil in 85% yield. $^{31}$P NMR (202 MHz, CD$_3$CN) δ 146.84; ESI-QQQ-calc. for $C_{26}H_{44}N_3O_3P$ 494.6 (+H$^+$); found 494.4.

Scheme 2 illustrates a synthetic scheme for the preparation of 5'-activated cyclooctyne nucleoside phosphoramidites with cleavable linkers, which may be used as a last nucleoside during the oligonucleotide synthesis to provide a handle for the click reaction to facilitate the purification of the complete sequences. While this scheme uses thymidine base as an example, other bases (with proper protections) can also be synthesized in a similar manner.

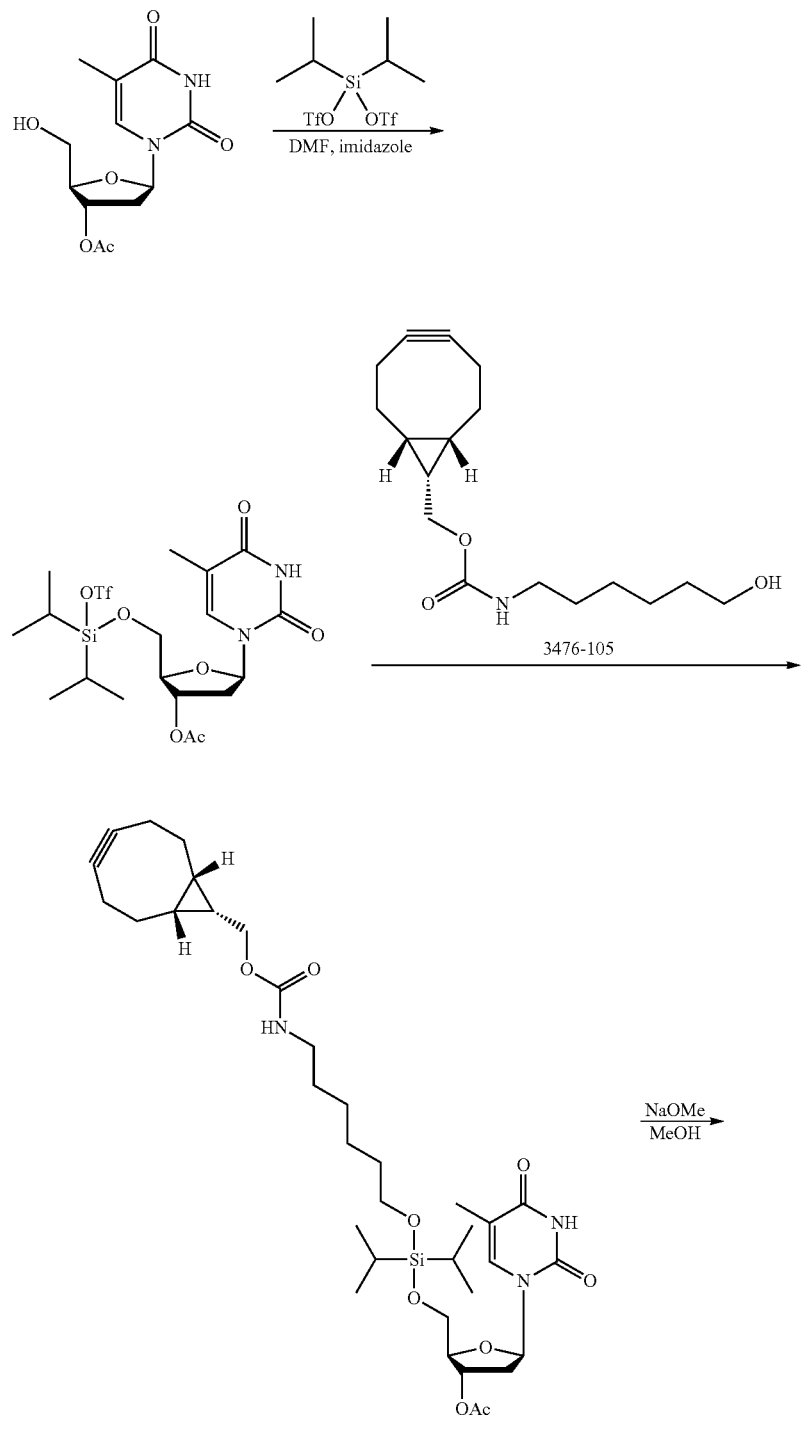

Scheme 2. Synthesis of a 5'-constrained cyclooctyne nucleoside phosphoramidite with a cleavable linker

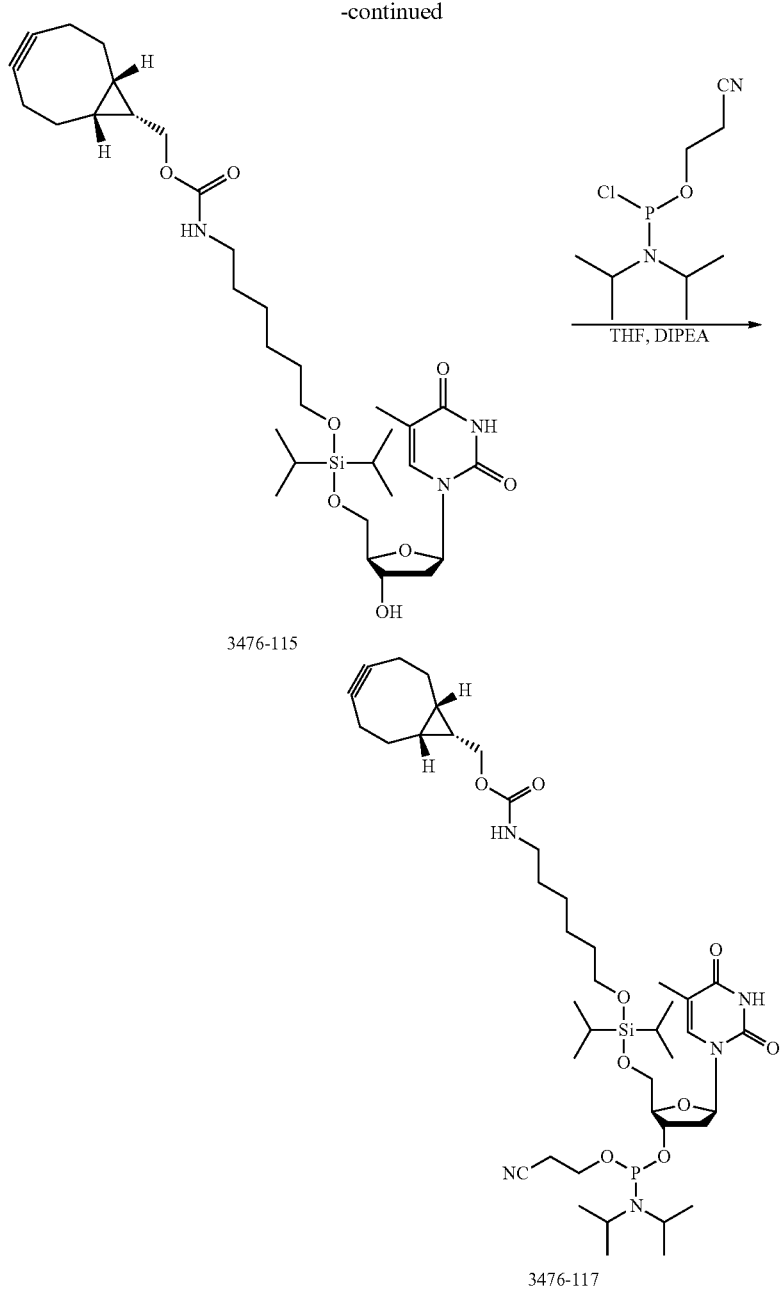

3476-115

3476-117

As shown in Scheme 2, the synthesis of the desired phosphoramidites use common organic reaction. One skilled in the art would be able to carry out these reactions without difficulty. As an illustration, detailed procedures and reaction conditions for the synthesis of compound 3476-117 are described below.

Synthesis of Compound 3476-112

Diisopropylsilyl ditriflate (1.04 mL, 0.00352 mol) was dissolved in DMF (15 mL) under $N_2$ and cooled to −42° C. This was followed by the drop wise addition of 3'-OAc-dT (1 g, 0.00352 mol) in DMF (10 mL). This was followed by the addition of imidazole (0.480 g, 0.00704 mol) in DMF (5 mL). The reaction was allowed to continue until all of the diisopropylsilyl ditriflate material had been consumed as judged by TLC (1 h). It was then warmed to room temperature 3476-105 in DMF (5 mL) was added drop wise. The reaction was then stirred until completion as judged by TLC (30 min). Upon completion, the solvent was removed under reduced pressure and the residue was taken up in DCM and washed with saturated sodium bicarbonate. The organic layer was extracted, dried over sodium sulfate, filtered and evaporated in vacuo. The residue was then purified by column chromatography using a gradient up to 3% MeOH in DCM. The final compound was obtained as a white foam in quantitative yield.
$^1$H NMR (500 MHz, $CDCl_3$) δ 9.03 (1H, s), 7.53 (1H, s), 6.36 (1H, t), 5.32 (1H, d), 4.80 (1H, d), 3.94-4.05 (5H, m), 3.74 (2H, t), 3.12-3.17 (2H, m), 2.36-2.42 (3H, m), 2.16-2.29 (2H, m), 2.09-2.14 (6H, m), 1.90 (s, 3H), 1.47-1.57 (4H, m), 1.32-1.38 (6H, m), 1.01-1.05 (14H, m), 0.65-0.72 (3H, m); $^{13}$C NMR (126 MHz, CDCl$_3$) δ 209.1, 207.9, 162.5, 156.84, 135.14, 130.48, 110.00, 98.77, 68.90, 67.63, 62.59, 45.13, 41.56, 40.75, 39.16, 33.26, 32.54, 30.04, 29.97, 26.35, 25.38, 25.28, 23.74, 23.50, 22.78, 22.39, 21.80, 21.57, 21.36, 20.56; ESI-QQQ-calc. for C$_{35}$H$_{55}$N$_3$O$_9$Si 690.4 (+H$^+$); found 690.4.

Synthesis of Compound 3476-115

Compound 3476-112 (1 g) was dissolved in ethanol (10 mL). This was followed by a 1:1 mix of ammonia/methylamine (2 mL). The solution was then heated to 55° C. and allowed to stir for 30 min. Upon completion, volatiles were removed under high vacuum and the residual material was taken up in DCM. This was then washed with water. The organic layer was dried over sodium sulfated, filtered and evaporated in vacuo to give a yellowish oil. This material was then purified by column chromatography using a gradient of 50/50 EtOAc:hexanes→EtOAc and obtained as a white solid in quantitative yield. $^1$H NMR (500 MHz, CDCl$_3$) δ 9.20 (1H, s), 7.52 (1H, s), 6.35 (1H, t), 4.84 (1H, s), 4.50 (1H, s), 3.94-4.04 (5H, m), 3.73-3.75 (2H, t), 3.48 (1H, s), 3.12-3.17 (1H, m), 2.36-2.40 (2H, m), 2.23-2.29 (2H, m), 2.09-2.14 (2H, m), 1.90 (3H, s), 1.46-1.56 (4H, m), 1.32-1.35 (4H, m), 1.03-1.05 (14H, m), 0.65-0.73 (3H, m); $^{13}$C NMR (126 MHz, CDCl$_3$) δ 163.92, 157.00, 150.44, 135.58, 110.86, 98.78, 87.18, 84.92, 87.18, 84.92, 71.88, 69.09, 63.06, 40.99, 40.72, 33.26, 32.48, 29.91, 26.26, 25.28, 23.68, 22.81, 21.37, 17.39, 17.33, 17.30, 17.24, 12.47, 12.00, 11.84; C$_{33}$H$_{53}$N$_3$O$_8$Si 648.4 (+H$^+$); found 648.4.

Synthesis of Compound 3476-117

Compound 3476-115 (0.8 g, 0.00116 mol) was dissolved in THF (10 mL) under dry nitrogen. This was followed by the addition of DIPEA (0.85 mL, 0.00487 mol) and the drop wise addition of the diisopropylphosphorochloridate reagent (0.3 mL, 0.00128 mol). This reaction mixture was then stirred for 2 h until completion. It was then quenched with 5% aqueous sodium bicarbonate (5 mL) and diluted with DCM (200 mL). This mixture was then transferred to a separatory funnel and more 5% aqueous sodium bicarbonate (50 mL) was added. The aqueous layer was washed with DCM (100 mL) and the organic layers were pooled, dried over sodium sulfated, filtered, and evaporated in vacuo. The residual material was then purified by column chromatography using 3:2 EtOAc/hexanes with 2% TEA to give a white foam in 95% yield. $^{31}$P NMR (202 MHz, CD$_3$CN) δ 148.03, 147.98; ESI-QQQ-calc. for C$_{42}$H$_{70}$N$_5$O$_9$PSi 848.5 (+H$^+$); found 848.5.

As noted above, in accordance with embodiments of the invention, an azide or nitrone-containing solid support (e.g., beads or substrate) may be used to "click" and trap activated cyclooctyne-containing oligonucleotides, thereby facilitating the purification of the desired sequences. An azide or nitrone-containing solid support can be readily prepared using commercially available solid supports as shown in Scheme 3:

Scheme 3. Synthesis of azide containing controlled pore glass (CPG)

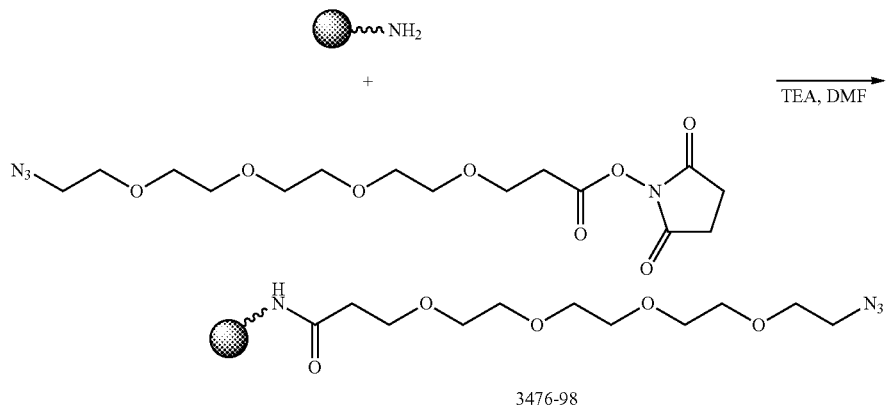

3476-98

While Scheme 3 uses controlled port glass beads as solid supports. Any other suitable solid supports may be used without departing from the scope of the invention, such as polymer or plastic beads, glass plates, or polymer or plastic plates. A linker with an azide compound is coupled to CPG that contains an amino linker. Other types of reactive functional groups on a solid support may also be used, such as —OH, —SH, —COOH, etc. As an example, a detailed procedure and conditions for the synthesis of reagent 3476-98 is illustrated below.

Synthesis of Compound 3476-98

1000 Å CPG (19.2 g, loading=103 umol/g, (lot #PSI0021624 purchased from Chemgenes, Wilmington, Mass.) was suspended in DMF (50 mL). This was followed by the addition of triethylamine (1.8 mL, 129 mol) and azido-Peg-NHS-ester. The reaction was then shaken for 16 h. Upon completion, it was filtered through a glass frit and washed with DCM, MeOH, and finally ether. The material was then dried under high vac. It was then treated with CAP A and CAP B (20 mL of each) for 15 min. It was again filtered and washed as above. The material was then dried under high vacuum.

Advantages of the invention may include one or more of the following. The cyclooctyne moiety itself can be prepared on large scale (e.g., Kg) and is cheap to synthesize. In addition, it will use much less consumables, such as solvents in the case of HPLC, polymerization, etc., and thus be a much greener process. The cyclooctyne moiety will be freely soluble in organic solvents (e.g., acetonitrile) and will allow rapid coupling times as a capping agent or nucleotide monomer. Upon cleavage of the oligonucleotide from the solid support, the cyclooctane-containing capped failures or cyclooctane containing full length product will undergo a rapid "click" reaction with an azide or nitrone containing solid support, covalently separating them out from the mixture. This is a major improvement over existing methods, where the purification step will be on the order of minutes instead of hours, greatly enhancing high throughput capability. In addition, because the click reaction is known to be near quantitative, this will greatly enhance yield and purity over existing methods, which is important on small or large scale. Furthermore, this platform will be applicable to a wide range of solvents and reaction conditions and will not be limited to certain conditions as in the case of affinity purification. The click reaction is also known to be very specific so there will be no modification of the oligonucleotide. Finally, this method will be especially useful for the purification of long oligonucleotides and not limited to shorter ones as in other prior art.

Synthesis of Azide-Containing Agarose Beads

Amino-derivatized agarose beads were filtered and lyophilized. They were then suspended in DMF and reacted with Azide-PEG4-NHS ester (purchased from Click chemistry tools) in the presence of triethylamine for 16 h at room temperature. Upon completion, the material was filtered, washed with DMF, MeOH, and ether. The material was then dried under high vac. It was then treated with CAP A and CAP B (20 mL of each) for 15 min. It was again filtered and washed as above. The material was then dried under high vacuum.

Synthesis of Oligonucleotides

Figure 6:
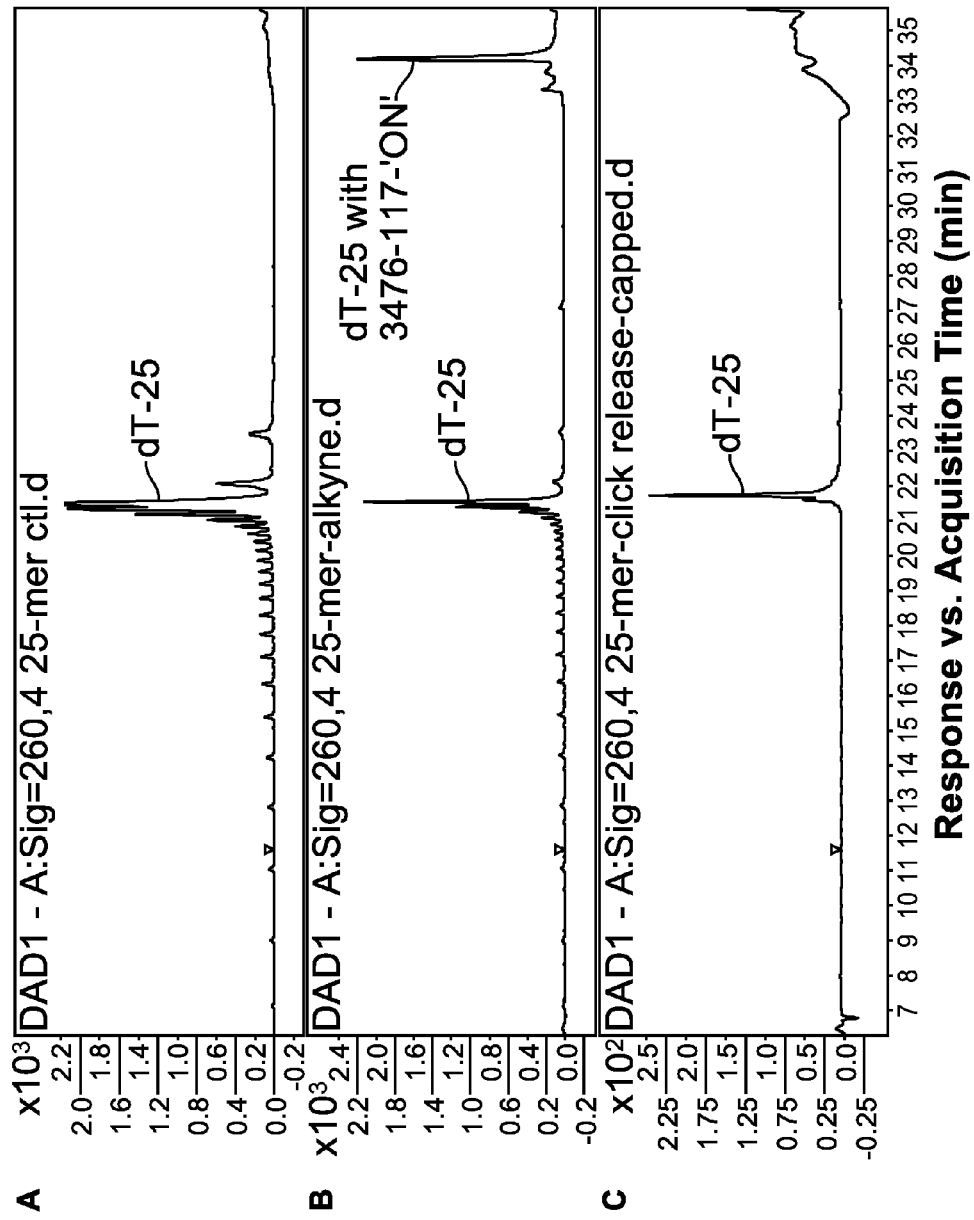
FIG. 6 shows three graphs (A) (B) and (C) showing the response versus acquisition time for three oligonucleotides.

A dT-25-mer oligonucleotide (1) was synthesized with 3476-117 added as the last base using standard DNA synthesis conditions (FIG. 6B). A dT-25-mer control (2) without 3476-117 was also synthesized for comparison (FIG. 6A). These oligo were then treated with ammonium hydroxide, 55° C., for 16 h, followed by lypholization. Compound (1) was further treated with the azide containing agarose beads in water overnight. The beads were then filtered, washed with water, and dried. They were then treated with 1 M TBAF for 8 h. The beads were filtered and the filtrate was diluted with water and passed through a G-25 sephadex column. This material was then analyzed by HLPC-MS (FIG. 6C). As evident, the oligo synthesized with 3476-117 (1) is extremely pure relative to the one without after treatment with azide-containing beads followed by release with fluoride ion.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:
1. A reagent for oligonucleotide synthesis or purification, wherein the reagent has a structure of:

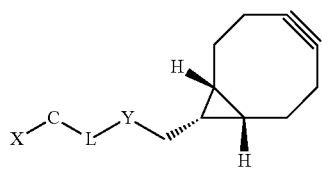

Formula (I)

wherein
X is a phosphoramidite group, an H-phosphonate group, an acetal group, or an isocyanate;
C is a direct bond or a cleavable adaptor wherein the cleavable adaptor is represented by —$C_a$—$C_b$—, wherein $C_a$ is connected to X and is a direct bond, hydrocarbyl, aryl, heteroaryl, cycloalkyl, heterocyclyl, a nucleoside, each of which is optionally substituted with one to two substituents selected from halo, hydroxyl, ($C_1$-$C_6$) alkoxy, ($C_1$-$C_6$) alkyl, amino or alklyamino; $C_b$ is a direct bond, a silanyl group, a trityl group, or a vicinyl alcohol group;
L is a hydrocarbyl chain which may be optionally substituted with one to four substituent groups independently selected from the group consisting of 5-to 9-membered heteroaryl, 4- to 9-membered heterocyclyl, amino, ether, carboxyl, carbamoyl, ($C_6$-$C_{12}$)aryl, —O—R", —O—CO—R", —NR'—R", —NR'—CO—R", —CO—NR'—R", —CO—R", —CN, halogen, or a combination thereof, wherein R' and R" are independently H or ($C_1$-$C_6$)hydrocarbyl; or
L is a hydrocarbyl chain interspersed with other atoms, as represented by —(CHR')$_a$—W$_b$—(CHR')$_c$—V$_d$—(CHR')$_e$—, wherein W and V are independently —O—, —S—, or —NR'—; R' is H or ($C_1$-$C_6$)alkyl; and a, b, c, d, and e are independently an integer from 0 to 10; and
Y is a linkage functional group selected from —O—, —S—, —NR'—, —NH—CO—O—, —O—CO—NH—, or —NH—CO—NH—, wherein R' is hydrogen or ($C_1$-$C_6$)hydrocarbyl.

2. The reagent of claim 1, wherein C is represented by —$C_a$—$C_b$—, wherein $C_a$ is connected to X and is a direct bond, ($C_1$-$C_{12}$)hydrocarbyl, ($C_6$-$C_{12}$)aryl, 5- to 12-membered heteroaryl, ($C_3$-$C_{12}$)cycloalkyl, 4- to 12-membered heterocyclyl, a nucleoside, each of which is optionally substituted with one to two substituents selected from halo, hydroxyl, ($C_1$-$C_6$) alkoxy, ($C_1$-$C_6$) alkyl, amino or alklyamino; $C_b$ is a direct bond, a silanyl group, a trityl group, or a vicinyl alcohol group.

3. The reagent of claim 1, wherein (1) L is a hydrocarbyl group selected from ($C_1$-$C_{12}$)alkyl, ($C_2$-$C_{12}$)alkenyl, or ($C_2$-$C_{12}$)alkynyl, each of which may be optionally substituted with a group selected from amino, ether, carboxyl, carbamoyl, or halogen; or (2) L is represented by a generic formula of —(CH$_2$)$_a$—W$_b$—(CH$_2$)$_c$—V$_d$—(CH$_2$)$_e$—, wherein W and V are independently —O—, —S—, or —NR'—, wherein R' is hydrogen or a lower alkyl; and a, b, c, d, and e are independently an integer from 0 to 10.

4. The reagent of claim 1, wherein X is the phosphoramidite group and the reagent has a structure represented by Formula (II):

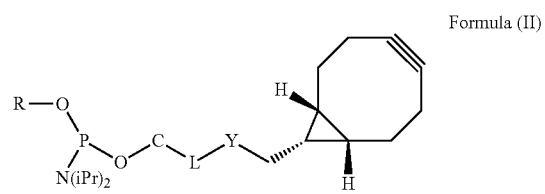

Formula (II)

wherein R is ($C_1$-$C_6$)alkyl or cyanoethyl.

5. The reagent of claim 1, wherein X is the H-phosphonate group and the reagent has a structure represented by Formula (III):

Formula (III)
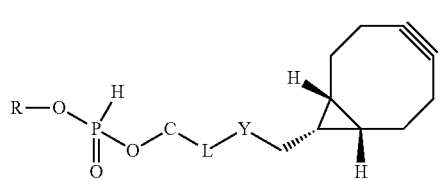
wherein $R_1$ is $(C_1\text{-}C_6)$alkyl or cyanoethyl.
6. The reagent of claim 1, wherein X is the isocyanate group and the reagent has a structure represented by Formula (IV):
Formula (IV)
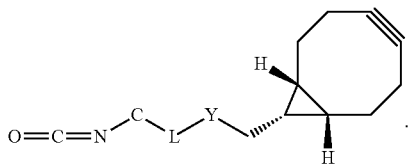
7. The reagent of claim 1, wherein Y is —O— and L is —$(CH_2)_n$—NH—CO—, wherein n is an integer from 2 to 10.
8. The reagent of claim 1, wherein the reagent is:
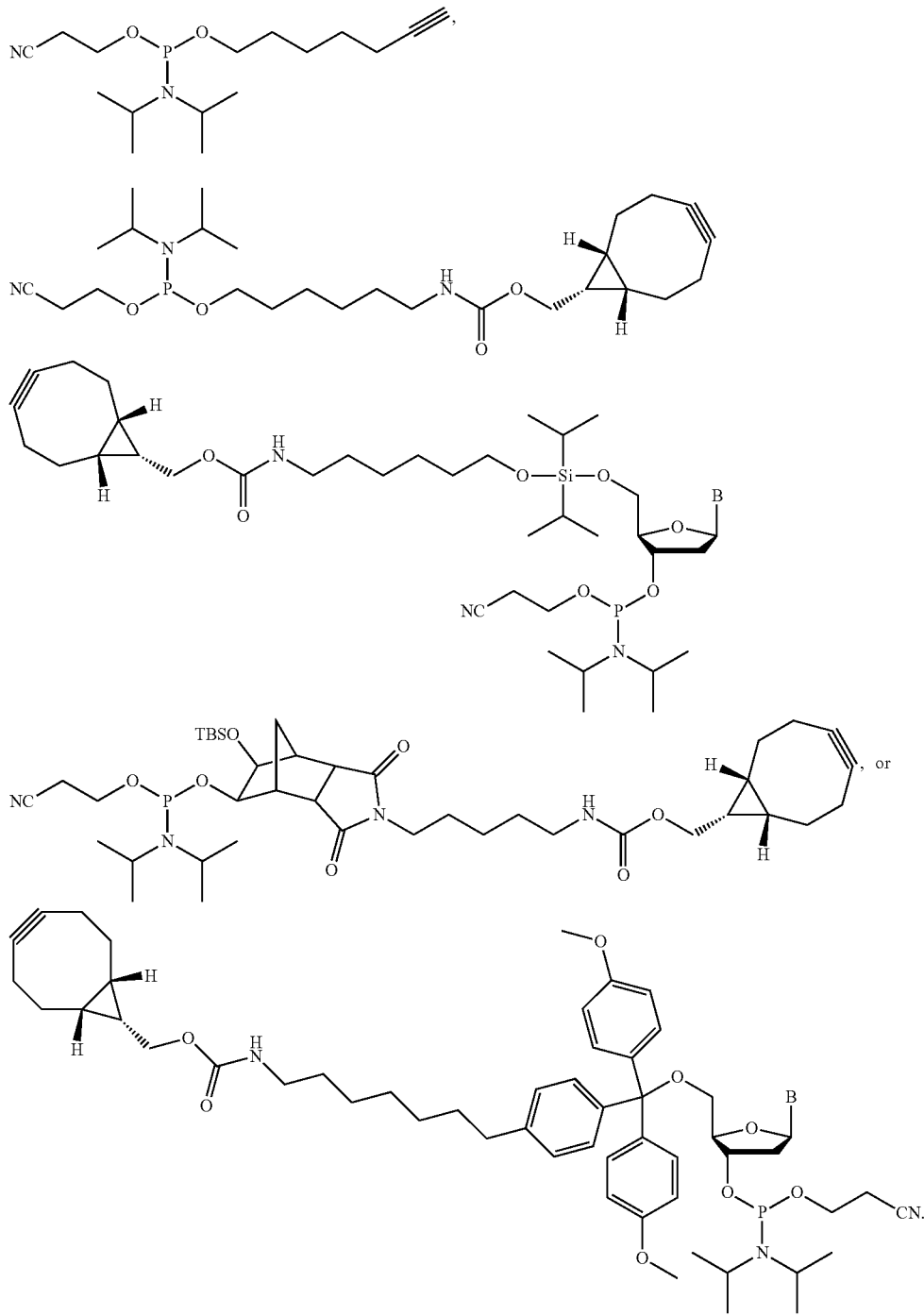

9. A method for synthesizing a polynucleotide, comprising:
   (a) deprotecting a 5'-hydroxy protecting group of an oligonucleotide on a solid support to produce a free 5'-hydroxy group of the oligonucleotide on the solid support;
   (b) coupling a nucleotide monomer, which contains a 5'-hydroxy protecting group, to the free 5'-hydroxy group of the oligonucleotide on the solid support via a 3'-phosphorous containing group on the nucleotide monomer;
   (c) capping unreacted 5'-hydroxy group of the oligonucleotide on the solid support using a capping agent; and
   (d) repeating steps (a)-(c) for a selected number of times to produce a polynucleotide on the solid support;
   wherein the capping agent has a structure of:

—X—C—L—H  (Formula A)

wherein
   X is a phosphoramidite group, an H-phosphonate group, an acetal group, or an isocyanate;
   C is a direct bond or a cleavable adaptor wherein the cleavable adaptor is represented by —$C_a$—$C_b$—, wherein $C_a$ is connected to X and is a direct bond, hydrocarbyl, aryl, heteroaryl, cycloalkyl, heterocyclyl, a nucleoside, each of which is optionally substituted with one to two substituents selected from halo, hydroxyl, ($C_1$-$C_6$) alkoxy, ($C_1$-$C_6$) alkyl, amino or alklyamino;
   $C_b$ is a direct bond, a silanyl group, a trityl group, or a vicinyl alcohol group;
   L is a hydrocarbyl chain which may be optionally substituted with one to four substituent groups independently selected from the group consisting of 5-to 9-membered heteroaryl, 4- to 9-membered heterocyclyl, amino, ether, carboxyl, carbamoyl, ($C_6$-$C_{12}$)aryl, —O—R", —O—CO—R", —NR'—R", —NR'—CO—R", —CO—NR'—R", —CO—R", —CN, halogen, or a combination thereof, wherein R' and R" are independently H or ($C_1$-$C_6$)hydrocarbyl; or
   L is a hydrocarbyl chain interspersed with other atoms, as represented by —(CHR')$_a$—W$_b$—(CHR')$_c$—V$_d$—(CHR')$_e$—, wherein W and V are independently —O—, —S—, or —NR'—; R' is H or ($C_1$-$C_6$)alkyl; and a, b, c, d, and e are independently an integer from 0 to 10; and
   H is a terminal alkyne or an activated cyclooctyne.

10. The method of claim 9, wherein the capping agent is represented by Formula (I)

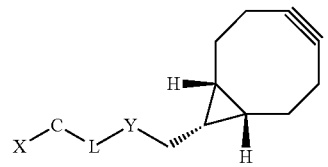

Formula (I)

wherein Y is a linkage functional group selected from —O—, —S—, —NR'—, —NH—CO—O—, —O—CO—NH—, or —NH—CO—NH—, wherein R' is hydrogen or ($C_1$-$C_6$)hydrocarbyl.

11. The method of claim 10, wherein X of Formula (I) is a phosphoramidite group represented by —P(OR$^{13}$)(NR$^{14}$R$^{15}$), wherein R$^{13}$ is cyanoethyl, and each of R$^{14}$ and R$^{15}$ is independently a ($C_1$-$C_6$)alkyl.

12. The method of claim 9, wherein the capping agent is:

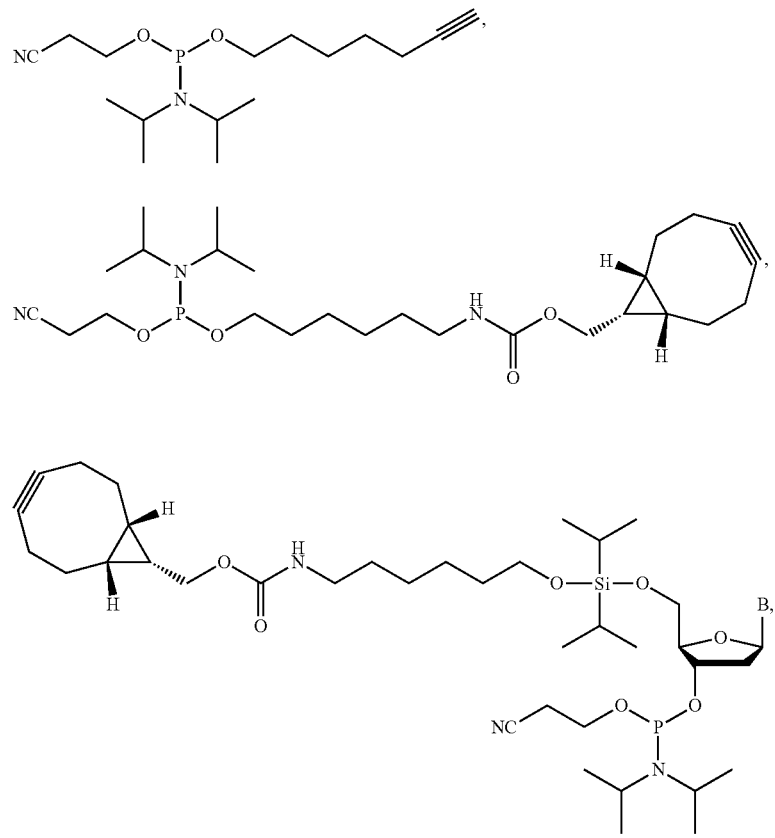

-continued

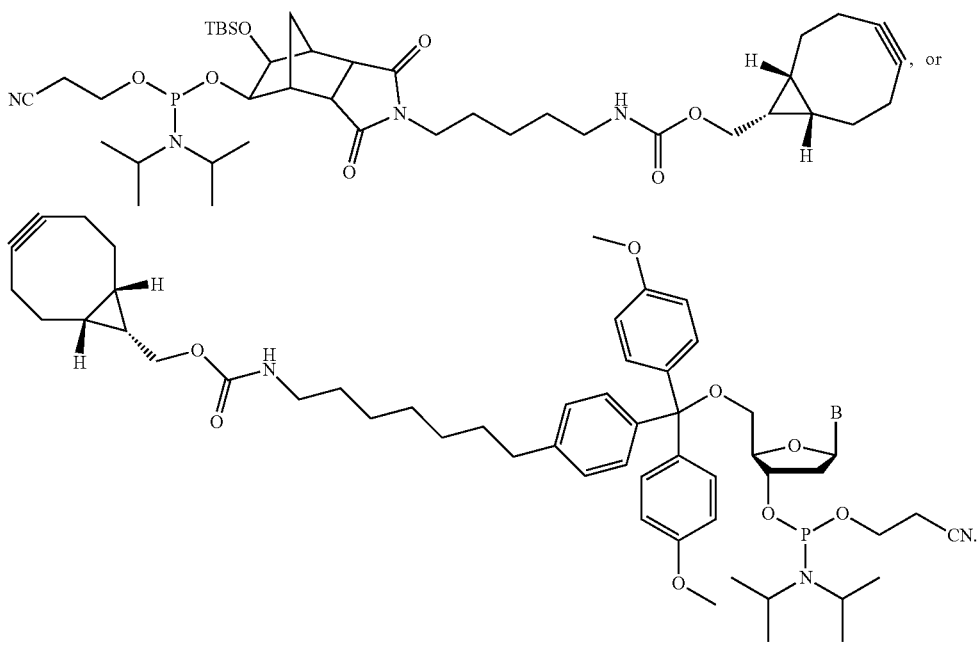

13. The method of claim 9, further comprising:
    (e) deprotecting and cleaving the polynucleotide from the solid support to produce a product mixture;
    (f) reacting a solution of the product mixture with an azide-containing solid support or a nitrone-containing solid support; and
    (g) separating the solution containing the polynucleotide from the solid support.

14. A method for synthesizing a polynucleotide, comprising:
    (a) deprotecting a 5'-hydroxy protecting group of an oligonucleotide on a solid support to produce a free 5'-hydroxy group of the oligonucleotide on the solid support;
    (b) coupling a nucleotide monomer, which contains a 5'-hydroxy protecting group, to the free 5'-hydroxy group of the oligonucleotide on the solid support via a 3'-phosphorous containing group on the nucleotide monomer;
    (c) capping unreacted 5'-hydroxy group of the oligonucleotide on the solid support using a capping reagent;
    (d) repeating steps (a)-(c) for a selected number of times to produce an intermediate polynucleotide on the solid support;
    (e) deprotecting a 5'-hydroxy protecting group on the intermediate polynucleotide; and coupling a final monomer to the intermediate polynucleotide to produce a final polynucleotide, wherein the final monomer contains a reagent of Formula (I):

Formula (I)

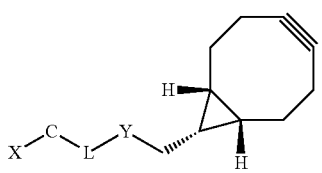

wherein

X is a phosphoramidite group, an H-phosphonate group, an acetal group, or an isocyanate;

C is a direct bond or a cleavable adaptor wherein the cleavable adaptor is represented by —$C_a$—$C_b$—, wherein $C_a$ is connected to X and is a direct bond, hydrocarbyl, aryl, heteroaryl, cycloalkyl, heterocyclyl, a nucleoside, each of which is optionally substituted with one to two substituents selected from halo, hydroxyl, ($C_1$-$C_6$) alkoxy, ($C_1$-$C_6$) alkyl, amino or alklyamino;

$C_b$ is a direct bond, a silanyl group, a trityl group, or a vicinyl alcohol group;

L is a hydrocarbyl chain which may be optionally substituted with one to four substituent groups independently selected from the group consisting of 5- to 9-membered heteroaryl, 4- to 9-membered heterocyclyl, amino, ether, carboxyl, carbamoyl, ($C_6$-$C_{12}$)aryl, —O—R", —O—CO—R", —NR'—R", —NR'—CO—R", —CO—NR'—R", —CO—R", —CN, halogen, or a combination thereof, wherein R' and R" are independently H or ($C_1$-$C_6$)hydrocarbyl; or L is a hydrocarbyl chain interspersed with other atoms, as represented by —(CHR')$_a$—W$_b$—(CHR')$_c$—V$_d$—(CHR')$_e$—, wherein W and V are independently —O—, —S—, or —NR'—; R' is H or ($C_1$-$C_6$)alkyl; and a, b, c, d, and e are independently an integer from 0 to 10; and Y is a linkage functional group selected from —O—, —S—, —NR'—, —NH—CO—O—, —O—CO—NH—, or —NH—CO—NH—, wherein R' is hydrogen or ($C_1$-$C_6$)hydrocarbyl.

15. The method of claim 14, wherein X in Formula (I) is an H-phosphonate group or a phosphoramidite group.

16. The method of claim 14, wherein the reagent is:

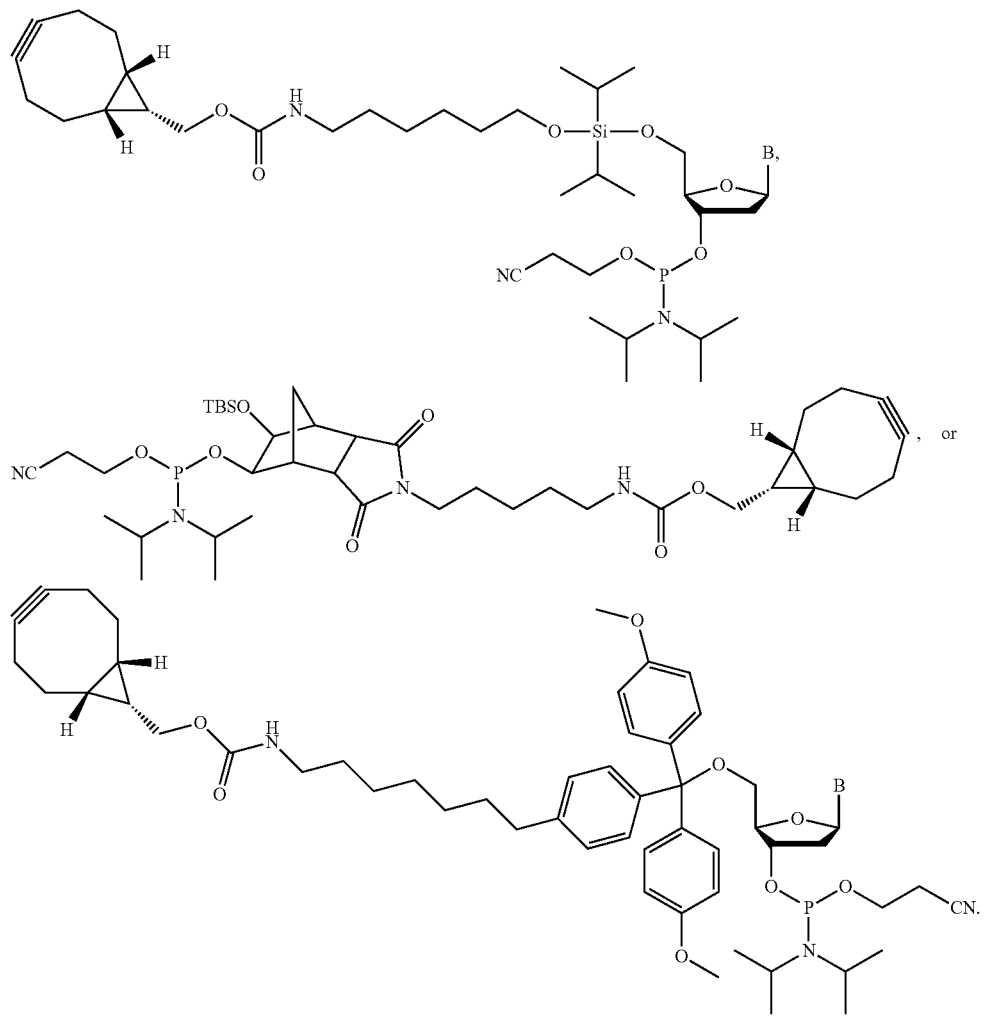

17. The method of claim 14, further comprising:
(f) deprotecting and cleaving the final polynucleotide from the solid support to produce a product mixture;
(g) reacting a solution of the product mixture with an azide-containing solid support or a nitrone-containing solid support to produce a full-length polynucleotide bonded to said azide-containing or nitrone-containing solid support; and
(h) isolating the full-length polynucleotide bonded to said azide-containing or nitrone-containing solid support.

* * * * *

UNITED STATES PATENT AND TRADEMARK OFFICE
CERTIFICATE OF CORRECTION

PATENT NO. : 8,889,851 B2  
APPLICATION NO. : 13/670220  
DATED : November 18, 2014  
INVENTOR(S) : Emily Marine Leproust et al.

Page 1 of 2

It is certified that error appears in the above-identified patent and that said Letters Patent is hereby corrected as shown below:

On the Title Page,

Item (56), in column 1, under "Other Publications", line 3, delete "Phosphoramidlte." and insert -- Phosphoramidite. --, therefor.

Item (56), in column 1, under "Other Publications", line 4, delete "Oligoribonucieic" and insert -- Oligoribonucleic --, therefor.

Item (56), in column 1, under "Other Publications", line 5, delete "Cyclooctne" and insert -- Cyclooctene --, therefor.

Item (56), in column 2, under "Other Publications", line 23, delete "Nurleotides," and insert -- Nucleotides, --, therefor.

In the Claims,

In column 36, line 10, In Claim 1, delete "alklyamino;" and insert -- alkylamino; --, therefor.

In column 36, line 15, In Claim 1, delete "5-to" and insert -- 5- to --, therefor.

In column 36, line 23-24, In Claim 1, delete "—(CHR')c—," and insert -- —(CHR')e—, --, therefor.

In column 36, line 37-38, In Claim 2, delete "alklyamino;" and insert -- alkylamino; --, therefor.

In column 37, line 9, In Claim 5, delete "R1" and insert -- R --, therefor.

In column 39, line 16, In Claim 9, delete "—X" and insert -- X --, therefor.

Signed and Sealed this  
Thirtieth Day of June, 2015

Michelle K. Lee  
*Director of the United States Patent and Trademark Office*

CERTIFICATE OF CORRECTION (continued)
U.S. Pat. No. 8,889,851 B2

In column 39, line 27, In Claim 9, delete "alklyamino;" and insert -- alkylamino; --, therefor.

In column 39, line 32, In Claim 9, delete "5-to" and insert -- 5- to --, therefor.

In column 40, line 7-8, In Claim 9, delete "—(CHR')$_c$—," and insert -- —(CHR')$_e$—, --, therefor.

In column 42, line 40, In Claim 14, delete "alklyamino;" and insert -- alkylamino; --, therefor.

In column 42, line 46, In Claim 14, delete "5-to" and insert -- 5- to --, therefor.